(12) United States Patent
Wong et al.

(10) Patent No.: US 9,192,322 B2
(45) Date of Patent: Nov. 24, 2015

(54) MAPPING VASCULAR PERFUSION TERRITORIES USING MAGNETIC RESONANCE IMAGING

(75) Inventors: Eric C. Wong, Del Mar, CA (US); Jia Guo, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 487 days.

(21) Appl. No.: 13/454,017

(22) Filed: Apr. 23, 2012

(65) Prior Publication Data

US 2012/0271157 A1 Oct. 25, 2012

Related U.S. Application Data

(60) Provisional application No. 61/478,344, filed on Apr. 22, 2011.

(51) Int. Cl.
 *A61B 5/05* (2006.01)
 *A61B 5/055* (2006.01)
 *A61B 5/00* (2006.01)

(52) U.S. Cl.
 CPC .............. *A61B 5/055* (2013.01); *A61B 5/0042* (2013.01)

(58) Field of Classification Search
 USPC .................... 600/407, 419, 410; 382/128; 324/306–308
 See application file for complete search history.

(56) References Cited

U.S. PATENT DOCUMENTS

| | | | |
|---|---|---|---|
| 5,766,128 A * | 6/1998 | Halamek et al. | 600/410 |
| 6,242,906 B1 * | 6/2001 | Andermo | 324/202 |
| 6,271,665 B1 | 8/2001 | Berr et al. | |
| 6,564,080 B1 | 5/2003 | Kimura | |
| 7,545,141 B2 | 6/2009 | Kimura | |
| 7,587,233 B2 | 9/2009 | Wong et al. | |
| 8,195,274 B2 | 6/2012 | Wong | |
| 2002/0099295 A1 * | 7/2002 | Gil et al. | 600/476 |
| 2004/0030240 A1 | 2/2004 | Kimura | |
| 2004/0044281 A1 | 3/2004 | Jesberger et al. | |
| 2004/0162483 A1 | 8/2004 | Kimura | |
| 2005/0277825 A1 | 12/2005 | Wong et al. | |
| 2005/0277828 A1 | 12/2005 | Alsop | |

(Continued)

FOREIGN PATENT DOCUMENTS

| | | |
|---|---|---|
| JP | 2005-305151 A | 11/2005 |
| WO | 03/094725 A1 | 11/2003 |

(Continued)

OTHER PUBLICATIONS

Introduction to nuclear magnetic resonance (NMR/MRI), J. Fessler, Oct. 28, 2009 11:28 (student version).*

(Continued)

*Primary Examiner* — Joel F Brutus
(74) *Attorney, Agent, or Firm* — Perkins Coie LLP

(57) ABSTRACT

Techniques, systems computer program products are disclosed for mapping of vascular perfusion territories by applying a train of pseudo-continuous radio frequency tagging pulses to modulate a first magnetization of one or more blood vessels that supply blood to one or more vascular perfusion territories, applying an encoding scheme using unipolar transverse gradient pulses to modulate a second magnetization of blood vessels of the vascular perfusion territories, obtaining efficiency for each blood vessel based on the applied encoding scheme and separating the vascular perfusion territories by using the obtained tagging efficiency in a decoding process.

16 Claims, 23 Drawing Sheets

(56) References Cited

U.S. PATENT DOCUMENTS

| | | | |
|---|---|---|---|
| 2006/0100503 A1 | 5/2006 | Takai et al. | |
| 2006/0161060 A1 | 7/2006 | Pai | |
| 2006/0184007 A1 | 8/2006 | Judd et al. | |
| 2007/0135712 A1* | 6/2007 | Maschke | 600/433 |
| 2007/0282193 A1 | 12/2007 | Brown | |
| 2008/0269595 A1* | 10/2008 | Wong | 600/411 |
| 2009/0088626 A1 | 4/2009 | Sutton et al. | |
| 2009/0245607 A1 | 10/2009 | Sugiura | |
| 2009/0274356 A1* | 11/2009 | Ying | 382/131 |
| 2010/0030062 A1 | 2/2010 | Bolar et al. | |
| 2010/0240983 A1 | 9/2010 | Jung et al. | |
| 2012/0268126 A1 | 10/2012 | Guo et al. | |
| 2013/0096418 A1 | 4/2013 | Jung et al. | |

FOREIGN PATENT DOCUMENTS

| | | |
|---|---|---|
| WO | 03/094728 A1 | 11/2003 |
| WO | 2010/108161 A2 | 9/2010 |
| WO | 2011/130581 A2 | 10/2011 |
| WO | 2012/145687 A2 | 10/2012 |

OTHER PUBLICATIONS

Quantitative imaging of perfusion using a single subtraction (QUIPSS and QUIPSS II), Buxton et al (provided by Applicant in the IDS).*
Wong, E.C., et al., "Velocity Selective Arterial Spin Labeling using an Adiabatic Hyperecho Pulse Train," Proceedings of the International Society for Magnetic Resonance in Medicine, 11:2181, (2003).
Wong, E.C., et al., "Velocity Selective Arterial Spin Labeling," Proceedings of the International Society for Magnetic Resonance in Medicine, 10:621, (2002).
Wu, W.C., et al., "A theoretical and experimental investigation of the tagging efficiency of pseudocontinuous arterial spin labeling," Magnetic Resonance in Medicine, 58(5):1020-1027, Nov. 2007.
Wu, W.C., et al., "The Effects of Flow Dispersion and Cardiac Pulsation in Arterial Spin Labeling," IEEE Transactions on Medical Imaging, 26(1):84-92, Jan. 2007.
Zaharchuk, G. et al., "Multislice perfusion and perfusion territory imaging in humans with separate label and image coils," Magnetic Resonance in Medicine, 41(6):1093-1098, Jun. 1999.
Zimine, I., et al., "Dual vessel arterial spin labeling scheme for regional perfusion imaging," Magnetic Resonance in Medicine, 56(5):1140-1144, Nov. 2006.
Alsop, D.C., et al., "Reduced transit-time sensitivity in noninvasive magnetic resonance imaging of human cerebral blood flow," Journal of Cerebral Blood Flow and Metabolism, 16(6):1236-1249, Nov. 1996.
Brookes, M.J., et al, "Noninvasive measurement of arterial cerebral blood volume using look-locker EPI and arterial spin labeling," Magnetic Resonance in Medicine, 58(1):41-54, Jul. 2007.
Buxton, R.B., et al., "A general kinetic model for quantitative perfusion imaging with arterial spin labeling," Magnetic Resonance in Medicine, 40(3):383-396, Sep. 1998.
Dai, W., et al., "Continuous Flow-Driven Inversion for Arterial Spin Labeling Using Pulsed Radio Frequency and Gradient Fields," Magnetic Resonance in Medicine, 60(6):1488-1497, Dec. 2008.
Davies, N.P., et al., "Selective arterial spin labeling (SASL): perfusion territory mapping of selected feeding arteries tagged using two-dimensional radiofrequency pulses," Magnetic Resonance in Medicine, 49(6):1133-1142, Jun. 2003.
Detre, J.A., et al., "Perfusion imaging," Magnetic Resonance in Medicine, 23(1):37-45, Jan. 1992.
Detre, J.A., et al., "Noninvasive Perfusion MR Imaging Using Spin Labeling Arterial Water," Chapter 15, Part V in Diffusion and Perfusion: Magnetic Resonance Imaging: Applications to Functional MRI (D. Le Bihan, Ed.), p. 296-305, Raven Press, New York, 1995.
Dixon, W.T., et al., "Projection angiograms of blood labeled by adiabatic fast passage," Magnetic Resonance in Medicine, 3(3):454-462, Jun. 1986.
Duyn, J.H., et al., "Simple correction method for k-space trajectory deviations in MRI," Journal of Magnetic Resonance, 132(1):150-153, May 1998.
Edelman, R.R. et al., "Qualitative mapping of cerebral blood flow and functional localization with echo-planar MR imaging and signal targeting with alternating radio frequency," Radiology, 192(2):513-520, Aug. 1994.
Garcia, D.M., et al., "Pseudo-continuous flow driven adiabatic inversion for arterial spin labeling," Proceedings 13th Scientific Meeting, International Society for Magnetic Resonance in Medicine, p. 37, (2005).
Garwood, M., et al., "Advances in Magnetic Resonance—The Return of the Frequency Sweep: Designing Adiabatic Pulses for Contemporary NMR," Journal of Magnetic Resonance, 153(2):155-177, Dec. 2001.
Garwood, M., et al., "Symmetric Pulses to Induce Arbitrary Flip Angles with Compensation for RF Inhomogeneity and Resonance Offsets," Journal of Magnetic Resonance, 94(3):511-525, Oct. 1991.
Gunther, M., "Efficient visualization of vascular territories in the human brain by cycled arterial spin labeling MRI," Magnetic Resonance in Medicine, 56(3):671-675, Sep. 2006.
Gunther, M., et al. "Single-shot 3D imaging techniques improve arterial spin labeling perfusion measurements," Magnetic Resonance in Medicine, 54(2):491-498, Aug. 2005.
Guo, J., et al., "Imaging of Oxygen Extraction Fraction Using Velocity Selective Excitation with Arterial Nulling (VSEAN)," Proceedings of the International Society for Magnetic Resonance in Medicine,18:4057, (2010).
Hendrikse, J., "Flow territory mapping of the cerebral arteries with regional perfusion MRI," Stroke, 35(4):882-887, Apr. 2004.
Hennig, et al., "Hyperechoes," Magnetic Resonance in Medicine, 46(1):6-12, Jul. 2001.
International Search Report and Written Opinion mailed on Dec. 21, 2011 for International Application No. PCT/US2011/032591, filed Apr. 14, 2011 (7 pages).
International Search Report and Written Opinion mailed on Nov. 30, 2012 for International Application No. PCT/US2012/034537, filed Apr. 20, 2012 (6 pages).
International Search Report and Written Opinion mailed on Nov. 30, 2012 for International Application No. PCT/US2012/034720, filed Apr. 23, 2012 (6 pages).
International Search Report and Written Opinion mailed on Oct. 22, 2010 for International Application No. PCT/US2010/028068, filed Mar. 19, 2010 (7 pages).
International Search Report and Written Opinion mailed on Sep. 15, 2003 for International Application No. PCT/US03/14978, filed May 13, 2003 (3 pages).
Jung, Y., et al., "Multi-phase pseudo-continuous arterial spin labeling (MP PCASL): Robust PCASL method for CBF quantification," Proceedings 17th Scientific Meeting, International Society for Magnetic Resonance in Medicine, p. 622, (2009).
Jung, Y., et al., "Multiphase pseudocontinuous arterial spin labeling (MP-PCASL) for robust quantification of cerebral blood flow," Magnetic Resonance in Medicine, 64(3):799-810, Sep. 2010.
Jung, Y., et al., "Pseudo-continuous arterial spin labeling with optimized tagging efficiency for quantitative ASL fMRI," Proceedings 17th Scientific Meeting, International Society for Magnetic Resonance in Medicine, p. 1578, (2009).
Kim, S.G., "Quantification of relative cerebral blood flow change by flow-sensitive alternating inversion recovery (FAIR) technique: Application to functional mapping," Magnetic Resonance in Medicine, 34(3):293-301, Sep. 1995.
Kim, S.G., et al., "Perfusion imaging by a flow-sensitive alternating inversion recovery (FAIR) technique: Application to functional brain imaging," Magnetic Resonance in Medicine, 37(3):425-435, Mar. 1997.
Kwong, K.K. et al., "Perfusion MR imaging," Proceedings of the Society of Magnetic Resonance, vol. 2, Second Meeting, Aug. 6-12, 1994, San Francisco, California, p. 1005.
Lagarias, J.C., et al., "Convergence properties of the nelder-mead simplex method in low dimensions," SIAM Journal on Optimization, 9(1):112-147, (1998).

(56) References Cited

OTHER PUBLICATIONS

Liu, T.T., et al., "A signal processing model for arterial spin labeling functional MRI," NeuroImage, 24(1):207-215, Jan. 2005.

Lu, K., et al., "Regional white matter perfusion measurement using an optimized pseudo-continuous ASL MRI," Proceedings 17th Scientific Meeting, International Society for Magnetic Resonance in Medicine, p. 1521, (2009).

Luh, W.M., et al, "Pseudo-continuous Arterial Spin Labeling at 7T," Proceedings 16th Scientific Meeting, International Society for Magnetic Resonance in Medicine, p. 3339, (2008).

Luh, W.M., et al., "QUIPSS II with thin-slice T1 Periodic Saturation: A Method for Improving Accuracy of Quantitative Perfusion Imaging Using Pulsed Arterial Spin Labeling," Magnetic Resonance in Medicine, 41(6):1246-1254, Jun. 1999.

Mildner, T., et al., "Continuous arterial spin labeling at the human common carotid artery: the influence of transit times," NMR in Biomedicine, 18(1):19-23, Feb. 2005.

Norris, D.G., et al., "Velocity Selective Radiofrequency Pulse Trains", Journal of Magnetic Resonance, 137 (1):231-236, Mar. 1999.

Paley, R.E.A.C., "On Orthogonal Matrices," Journal of Mathematics and Physics, 12:311-320, (1932-1933).

Parry, A. & P.M. Matthews, "Functional magnetic resonance imaging (fMRI): A 'window' into the brain," Oxford University, Centre for Functional Magnetic Resonance Imaging of the Brain (2002), 42 pages, Web site: http://www.fmrib.ox.ac.uk/fmri_intro/fmri_intro.htm [originally accessed on Aug. 20, 2003].

Sutton, B.P., et al., "Fast, iterative image reconstruction for MRI in the presence of field inhomogeneities," IEEE Transactions on Medical Imaging, 22(2):178-188, Feb. 2003.

Trampel, R., et al., "Efficiency of Flow-Driven Adiabatic Spin Inversion Under Realistic Experimental Conditions: A Computer Simulation," Magnetic Resonance in Medicine, 51(6):1187-1193, Jun. 2004.

Van Gelderen, P., et al., "Pittfalls of MRI measurement of white matter perfusion based on arterial spin labeling," Magnetic Resonance in Medicine, 59(4):788-795, Apr. 2008.

Wang, J., et al., "Amplitude-modulated continuous arterial spin-labeling 3.0-T perfusion MR imaging with a single coil: feasibility study," Radiology, 235(1):218-228, Apr. 2005.

Werner, R., et al., "Continuous artery-selective spin labeling (CASSL)," Magnetic Resonance in Medicine, 53(5):1006-1012, May 2005.

Williams, D.S., et al., "Magnetic resonance imaging of perfusion using spin inversion of arterial water," Proceedings of the National Academy of Sciences of the United States of America, 89(1):212-216, Jan. 1992.

Wong, E.C., "Vessel-encoded arterial spin-labeling using pseudocontinuous tagging," Magnetic Resonance in Medicine, 58(6):1086-1091, Dec. 2007.

Wong, E.C., "Vessel Encoded Arterial Spin Labeling Using Pseudo-Continuous Tagging," Proceedings of the International Society for Magnetic Resonance in Medicine, 14:668, (2006).

Wong, E.C., et al., "Blind detection of vascular sources and territories using random vessel encoded arterial spin labeling," Magnetic Resonance Materials in Physics, Biology and Medicine, 25(2):95-101, Apr. 2012.

Wong, E.C., et al., "Implementation of quantitative perfusion imaging techniques for functional brain mapping using pulsed arterial spin labeling," NMR in Biomedicine, 10(4-5):237-249, Jun.-Aug. 1997.

Wong, E.C., et al., "Quantitative imaging of perfusion using a single subtraction (QUIPSS and QUIPSS II)," Magnetic Resonance in Medicine, 39(5):702-708, May 1998.

Wong, E.C., et al., "Velocity-selective arterial spin labeling," Magnetic Resonance in Medicine, 55(6):1334-1341, Jun. 2006.

Wang, et al., "Arterial Transit Time Imaging with Flow Encoding Arterial Spin Tagging (FEAST)", Magnetic Resonance in Medicine, 50:599-607, 2003.

Elster, Allen D., "Flip (or Tip) Angle, What is meant by flip angle,?" Division of Radioiogic Sciences, Wake Forest School of Medicine, Questions and Answers in Magnetic Resonance Imaging, 2001, 1 page, Published online: URL Link: http://mri-q.com/what-is-flip-angle.html.

Mackiewich, B., "Basic Principles of MRI," University of British Columbia, MS Thesis, Aug. 19, 1995, "Intracranial Boundary Detection and Radio Frequency Correction in Magnetic Resonance Images," 3 pages, Published online: URL Link: https://www.cs.sfu.ca/~stella/papers/blairthesis/main/node11.html.

* cited by examiner

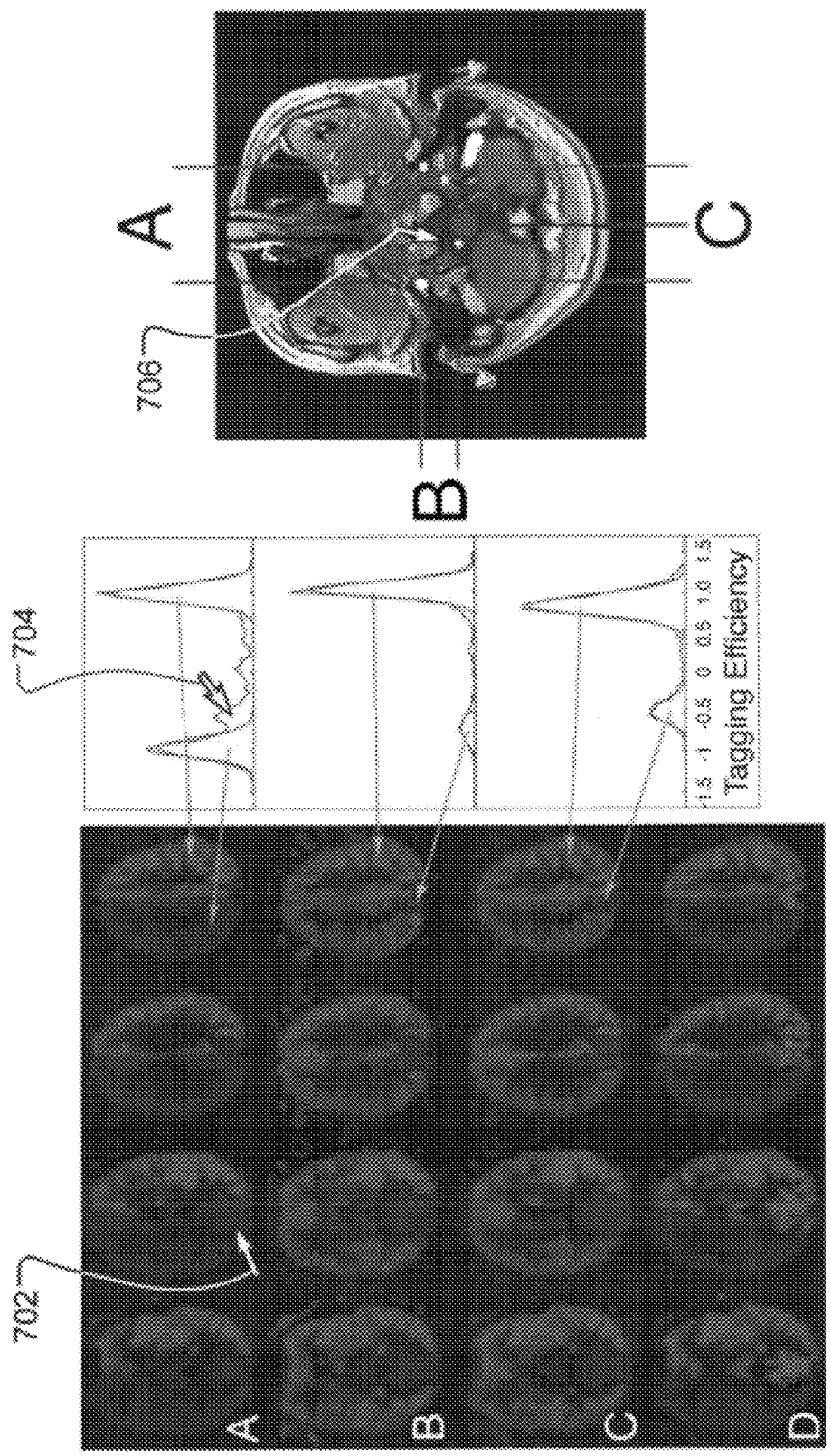

MAPPING VASCULAR PERFUSION TERRITORIES USING MAGNETIC RESONANCE IMAGING

CROSS-REFERENCE TO RELATED PATENT APPLICATIONS

This patent application claims the benefit of priority from the U.S. Provisional Patent Application 61/478,344, entitled "MAPPING VASCULAR PERFUSION TERRITORIES USING MAGNETIC RESONANCE IMAGING," filed on Apr. 22, 2011. The aforementioned provisional patent document is incorporated by reference in its entirety in the present patent document.

STATEMENT REGARDING FEDERALLY SPONSORED RESEARCH OR DEVELOPMENT

This invention was made with government support under EB002096 awarded by the National Institutes of Health. The government has certain rights in the invention.

BACKGROUND

This application relates to magnetic resonance imaging (MRI). Imaging through MRI techniques is well known and has been widely applied in imaging applications in medical, biological and other fields. A typical MRI technique produces an image of a selected body part of an object under examination by manipulating the magnetic spins in a body part and processing measured responses from the magnetic spins. An MRI system may include hardware to generate different magnetic fields for imaging, including a static magnetic field along a z-direction to polarize the magnetic spins, gradient fields along mutually orthogonal x, y, or z directions to spatially select a body part for imaging, and an RF magnetic field to manipulate the spins.

MRI techniques may be used to capture the functional changes in body parts or tissues such as the brain perfusion. One commonly-used technique for functional MRI is in vivo imaging by arterial spin labeling (ASL), where the arterial blood is tagged by magnetic inversion using RF pulses applied to a plane or slab of arterial blood proximal to the tissue of interest. Images are typically acquired with and without prior tagging of arterial blood and are subtracted to produce images that are proportional to perfusion. This magnetic tagging allows for the imaging of blood flow without the administration of dyes or other imaging agents. Hence, ASL provides non-invasive tagging in MRI measurements.

MRI techniques are often applied in situation in which locations of source vessels in the tagging plane are not known to a medical professional, requiring manual detection based on additional imaging or angiography.

Improvements to existing MRI techniques are needed.

SUMMARY

Techniques, systems and apparatus are disclosed that may be used for non-invasive mapping of perfusion territories and estimation of source vessel locations using MRI.

The subject matter described in this specification potentially can provide one or more of the following advantages associated with vessel encoded ASL imaging. For example, the described techniques can address an important clinical need to provide a general method to detect and identify sources of abnormal (collateral) routes of circulation regardless of their location, providing the clinician with important information for patient management. In clinical applications, the locations of some of the feeding arteries is typically known, but when there is vascular disease, which is the primary application of this class of imaging methods, there are often collateral routes of circulation that develop to perfuse the affected tissues. These collateral sources are often difficult to identify a priori. In addition, using unipolar vessel encoding gradient lobes can result in nearly complete insensitivity to resonance offsets at the tagging plane, and cam also provide a means for measuring the frequency offsets themselves.

Also, higher signal-to-noise ratio (SNR) can be achieved by using continuous rather than pulsed tagging. Better vessel selectivity can be obtained, as the vessel selection occurs within a single tagging plane through which the arteries are flowing. This is an improvement to the 3D slab or volume selective tag used in the pulsed methods that provide incomplete and spatially inhomogeneous separation of the feeding arteries. In addition, efficient and clear measurement can be obtained of the relative tagging efficiencies of each inflowing vessel, either for improved separation of the vessel encoded signal in post-processing, or for refined assignment of perfusion to a larger number of feeding arteries that there are encoding steps. Further, separation is possible of vascular territories above the Circle of Willis in the brain. While the volume and geometry of blood above the Circle of Willis renders pulsed methods extremely difficult, vessel encoded tagging within a single tagging plane can be efficient.

In one exemplary aspect a disclosed technique for mapping vascular perfusion territories includes applying a train of pseudo-continuous radio frequency tagging pulses to modulate a first magnetization of one or more blood vessels that supply blood to one or more vascular perfusion territories, applying an encoding scheme using unipolar transverse gradient pulses to modulate a second magnetization of blood vessels of the vascular perfusion territories, obtaining efficiency for each blood vessel based on the applied encoding scheme and separating the vascular perfusion territories by using the obtained tagging efficiency in a decoding process.

In another exemplary aspect, a disclosed method for estimating a location of at least one source vessel in a tagging plane of a subject includes applying a plurality of encoding steps in the tagging plane, each encoding step comprising application of gradient and radio frequency (RF) pulses to generate an MRI signal with modulation across the tagging plane, the MRI signal characterized by an orientation based on an orientation randomization scheme, a wavelength based on a wavelength randomization scheme and a phase based on a phase randomization scheme, acquiring a plurality of scan images based on the applied plurality of encoding steps, processing the acquired plurality of scan images to produce a processed data output and estimating, based on the processed data output, the location of the at least one source vessel.

The subject matter described in this specification can also be implemented as a system including a processor and a memory coupled to the processor. The memory may encode one or more programs that cause the processor to perform one or more of the method acts described in this specification. Further the subject matter described in this specification can be implemented using various MRI machines.

BRIEF DESCRIPTION OF THE DRAWINGS

FIG. 7A show an example of vessel encoded images from one subject.

FIG. 7B shows example histograms of the measured tagging efficiencies for each encoding scheme.

FIG. 7C shows example encoding locations.

Like reference symbols and designations in the various drawings indicate like elements.

DETAILED DESCRIPTION

Figure 1:
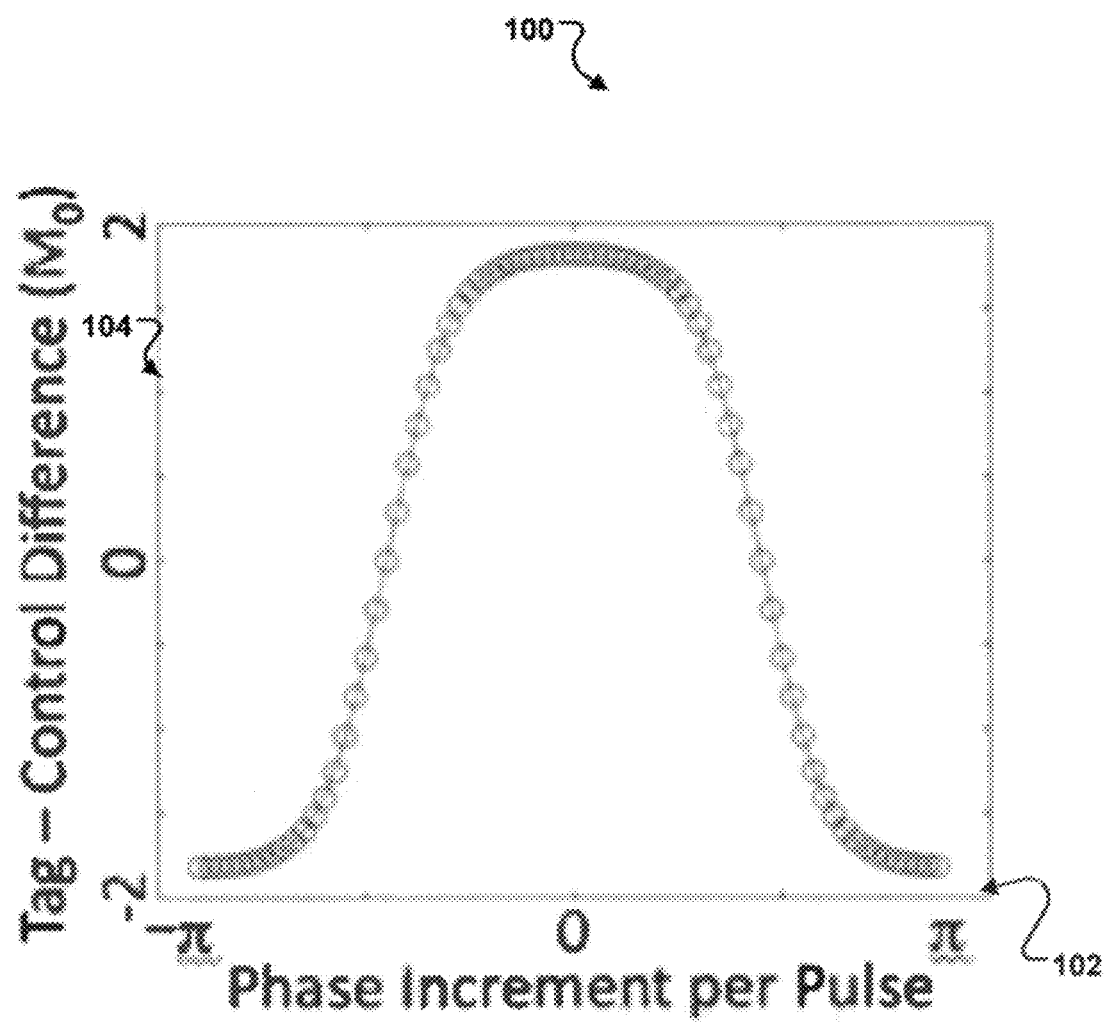
FIG. 1 shows a simulated response to unipolar VEASL tagging. After subtraction, paired encoding steps result in a dependence of arterial magnetization on the gradient related phase rotation.

The techniques and systems described in this application can enable non-invasive mapping of perfusion territories using MRI. In particular, a person can be placed in an MRI scanner, and without the use of any exogenous agents, map the tissue regions of the person that are supplied with blood from different feeding arteries.

In some implementations, unipolar gradient pulses may be used. In one advantageous aspect, the use of unipolar gradient pulses may help magnetize spins in a tagging plane in the same rotational direction (e.g., clockwise), thereby resulting in improved signal to noise ratios.

In some implementations, a random (non-uniform or uncorrelated) set of samples from the tagging plane may be acquired. Locations of source vessels may be estimated by comparing results obtained from the randomized tagging locations with a priori calculation results based on assumed vessel locations in the tagging plane. Using an optimization technique such as best correlation, numbers and locations of source vessels (e.g., feeding arteries) may be estimated using the randomized MRI signals.

Section headings are used in the DETAILED DESCRIPTION portion only to improve readability of the disclosed subject matter. The section headings do not in any way limit the scope of the disclosed and claimed subject matter.

Some disclosed implementations are within a class of MR imaging methods known as arterial spin labeling (ASL). There are pulsed ASL methods that tag the magnetization of arterial blood using short radiofrequency pulses, and continuous ASL methods that tag arterial blood using long trains of RF pulses and flow driven adiabatic inversion. Each of these classes of ASL methods includes sub-classes that allow for the tagging process to be selective for specific arteries. The two pulsed ASL and two continuous ASL methods are limited to imaging one perfusion territory at a time. In addition, there are two pulsed methods that may enable more time efficient encoding of perfusion data from two or more vessels simultaneously. Time efficiency of these methods can reduce the scan times from impractical (10-15 min) to practical (5 min) for various clinical applications. The present techniques and systems as described in this specification can improve vessel encoded ASL imaging.

In vascular territory imaging (VTI), blood in individual or groups of feeding arteries can be tagged using ASL, and images can be acquired that map the vascular distribution of those feeding arteries. Potential clinical applications for the mapping of vascular territories include the evaluation of vascular stenoses and the mapping of blood supplies to tumors. VTI can be performed sequentially for two or more vascular territories in order to develop a complete map of the blood supply to the target tissue.

Based on techniques described in this specification, multiple vascular territories can be mapped by tagging combinations of vessels in encoding schemes that enable efficient generation of vascular territory maps. The vessel encoded approach can be implemented based on pseudo-continuous tagging to provide high SNR tagging as well as good vessel selectivity and flexibility in tagging geometry.

Blind Detection of Source Vessel Locations and Resonance Offsets Using Randomly Encoded VEASL In one aspect, Techniques, apparatus and systems are described for efficiently estimating both the location and resonance offset of all feeding arteries in of Vessel Encoded Arterial Spin Labeling (VEASL) from randomly encoded data, allowing for identification of source vessels without prior knowledge of their locations. The method uses unipolar vessel encoding gradient lobes that provide the same encoding functionality as bipolar vessel encoding gradient lobes (see FIGS. 4-15 and accompanying description), results in nearly complete insensitivity to resonance offsets at the tagging plane. The techniques for using unipolar vessel encoding gradient lobes are based on the principles of decoding steps modified from the one disclosed below with respect to FIGS. 4-15, which use bipolar vessel encoding gradient lobes. Details of the decoding steps can be found in FIGS. 4-15 and in accompanying descriptions.

In vessel encoded ASL (VEASL), pseudo-continuous ASL tagging is used with additional gradient pulses applied across the tagging plane to encode the data with information about the location of the feeding arteries. In most implementations, prior information on the locations of feeding arteries in the tagging plane has been used to optimize the encoding process. However, in some cases, the relevant supplying arteries are not known ahead of time, as there may be variant or collateral circulation. In addition, the resonance offset in the tagging plane is known to affect the tagging efficiency, and can effectively be estimated and corrected using multiphase PCASL. An efficient method is described for estimating both the location and resonance offset of all feeding arteries in VEASL from randomly encoded data, allowing for identification of source vessels without prior knowledge of their locations.

Unipolar Gradient Pulses

In VEASL implementations, unipolar gradient pulses can be used between RF pulses to provide vessel encoding. This approach can combat a decrease or loss in tagging efficiency in the presence of resonance offsets in the tagging plane. Also, using unipolar gradient pulses for vessel encoding can provide the same functionality as using bipolar gradient pulses as described in the attached Appendix. Moreover, the use of unipolar vessel encoding gradient lobes can result in a simple shift of the encoding response with resonance offset without a loss of tagging efficiency. 60 pairs of encoding steps, with random orientation and wavelength λ, in addition to 2 pairs of non-vessel encoded steps, were used with imaging parameters. Each pair of encoding steps was 180° out of phase with one another, such that a difference signal between the pair removes static tissue signal and leaves a symmetrical dependence of the ASL signal upon vessel location, as shown in FIG. 1. The graph 100 shows the response plotted with horizontal axis 102 in units of phase increment per pulse and vertical axis 104 in units of Tag—control magnetization difference. The response calculated by Bloch simulation is shown as open circles, and a fit to the response, using three Fourier components is shown in solid line. The fitted curve was used in the data analysis. For an array of assumed vessel locations with 2 mm spacing, and resonance offsets with 11-22 Hz spacing, the expected ASL signal across encoding steps was calculated. This maps X and Y vessel coordinates and Frequency (XYF) space into 61 dimensional signal space. ASL data was acquired in healthy volunteers, and mapped from signal space back to XYF space. Clustering or other detection methods can be performed in either space, but in these examples clusters were identified in XYF space to determine the location and resonance offset of source vessels. These cluster centers were then used to generate the encoding matrix for a conventional linear analysis of the contribution of each vessel to the perfusion of each voxel (1).

Results

Figure 2:
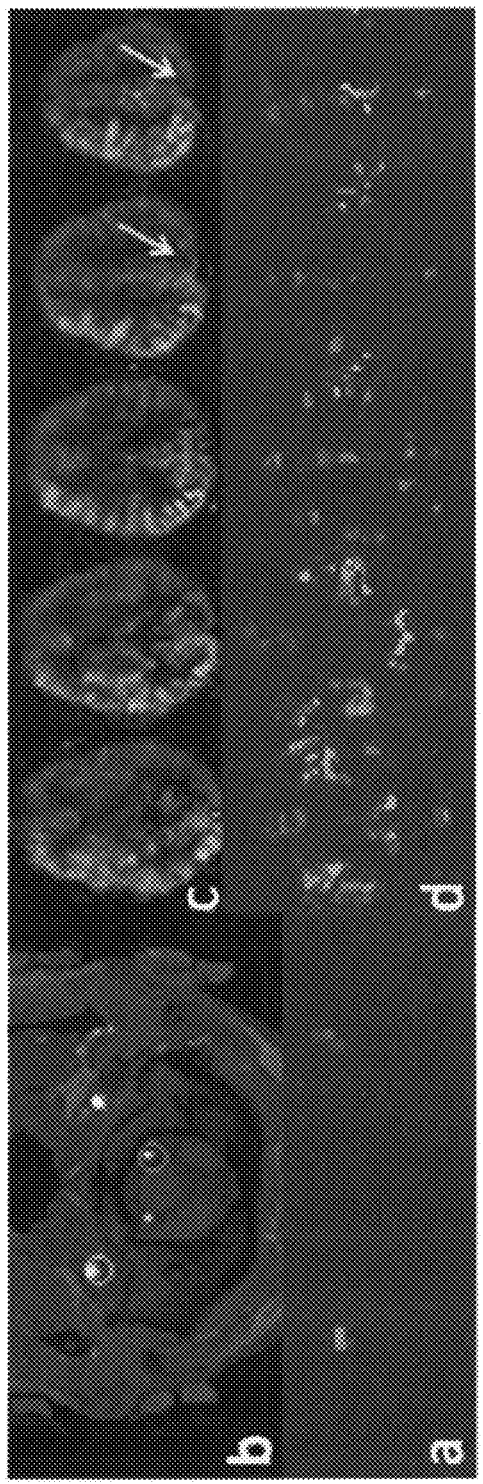
FIG. 2 is an image showing an exemplary tagging at inferior border of cerebellum (resonance offsets (L-R in Hz): 126, 58, 166): a) vessel locations detected by decoding ASL signal; (b) vessel locations overlaid on angiogram of tagging plane; (c) vascular territory maps generated using detected vessel locations, and (d) residual ASL signal not accounted for by detected vessels.
Figure 3:
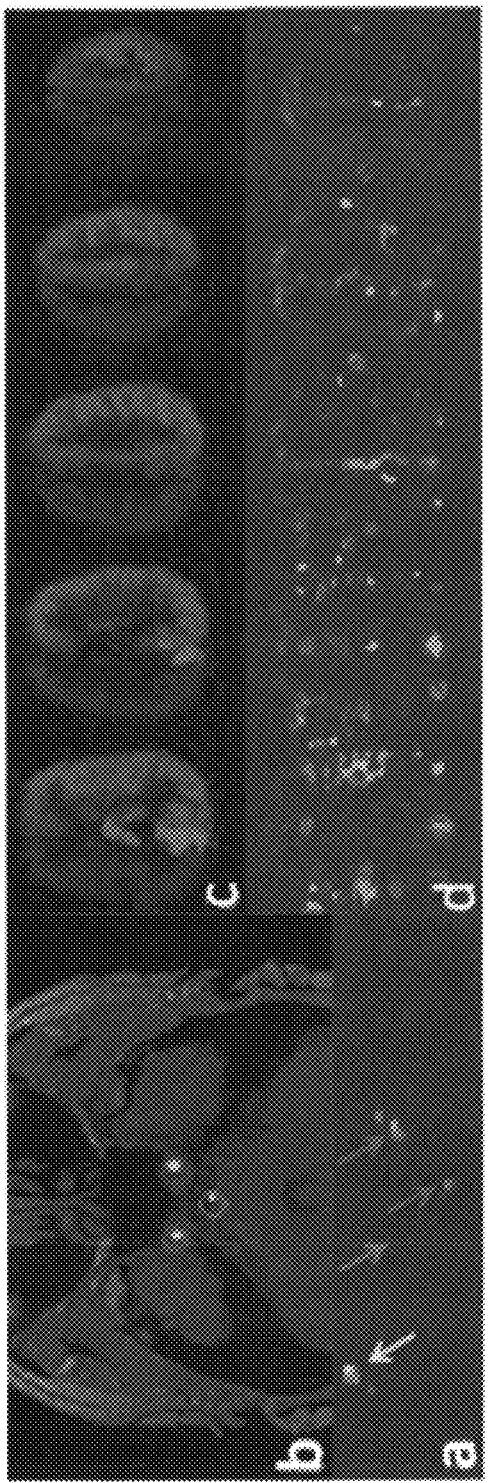
FIG. 3 is an image showing an exemplary tagging at midpons (resonance offsets (L-R in Hz): 126, 58, 166): a) vessel locations detected by decoding ASL signal; (b) vessel locations overlaid on angiogram of tagging plane; (c) vascular territory maps generated using detected vessel locations, and (d) residual ASL signal not accounted for by detected vessels.

Two examples are shown in FIGS. 2 and 3, using tagging planes through the vertebral arteries and pons, respectively. In the first example, separate clusters are detected for the left and right vertebral arteries (green and blue), suggesting incomplete mixing in the basilar artery, with more mixing higher in the posterior circulation (teal color, yellow arrows). Residual signal not accounted for by the four identified arteries follow a large artery distribution, suggesting cardiac pulsation as a dominant source of those components. At the level of the pons, only two of the three major arteries had a clear cluster in XYF space. Choosing any of the small clusters in the vicinity of the blue arrow results in a correct map (c), but detection of these clusters is not straightforward. A prominent cluster (yellow arrow), which does not correspond to a vessel location, dominates the residual signal (d), and is consistent with vascular pulsations. The resonance offsets at this level were large (58-166 Hz). With conventional single phase PCASL, at our tagging pulse spacing of 1.4 ms, the higher of these offsets would result in a tagging efficiency near zero.

Useful Tangible Applications

Working software on GE MRI scanner has been developed and experimental data has been collected in human subjects, demonstrating successful identification of feeding arteries without prior knowledge of their locations. Examples of useful tangible applications can include:

Diagnostic imaging in stroke.
Image based guidance for intra-arterial treatment of stroke.
Risk Assessment for stroke.
Evaluation of blood supply to tumors.
Evaluation of blood supply to organ transplants such as kidneys.
Evaluation of collateral blood supply in carotid or other cerebrovascular disease.

Various implementations have been described to identify vessel locations without prior knowledge despite large resonance offsets, using a random encoding strategy that provides unbiased sampling of the tagging plane and resonance offset space. This may be important for the detection of collateral supplies, which can flow through the tagging plane at unpredictable locations. At the level of the pons, the carotid and basilar arteries form a consistent triangle which appears amenable to 3 vessel encoding, but PCASL tagging at this location is usually problematic because of large resonance offsets.

In the current method the tagging is effectively multiphase pcasl at every location, but each location with a different random phase pattern. This results in consistent tagging efficiency and we suggest that this location may be a good default tagging location for VEASL of the left/right/posterior circulation. However, in the described data, not all vessels appear as distinct clusters, and some spurious clusters seem to represent vascular pulsations. Gating and longer post-labeling delays can be used to reduce these fluctuations, and post-processing methods can be used to identify and remove these non-localized fluctuations.

Figure 4:
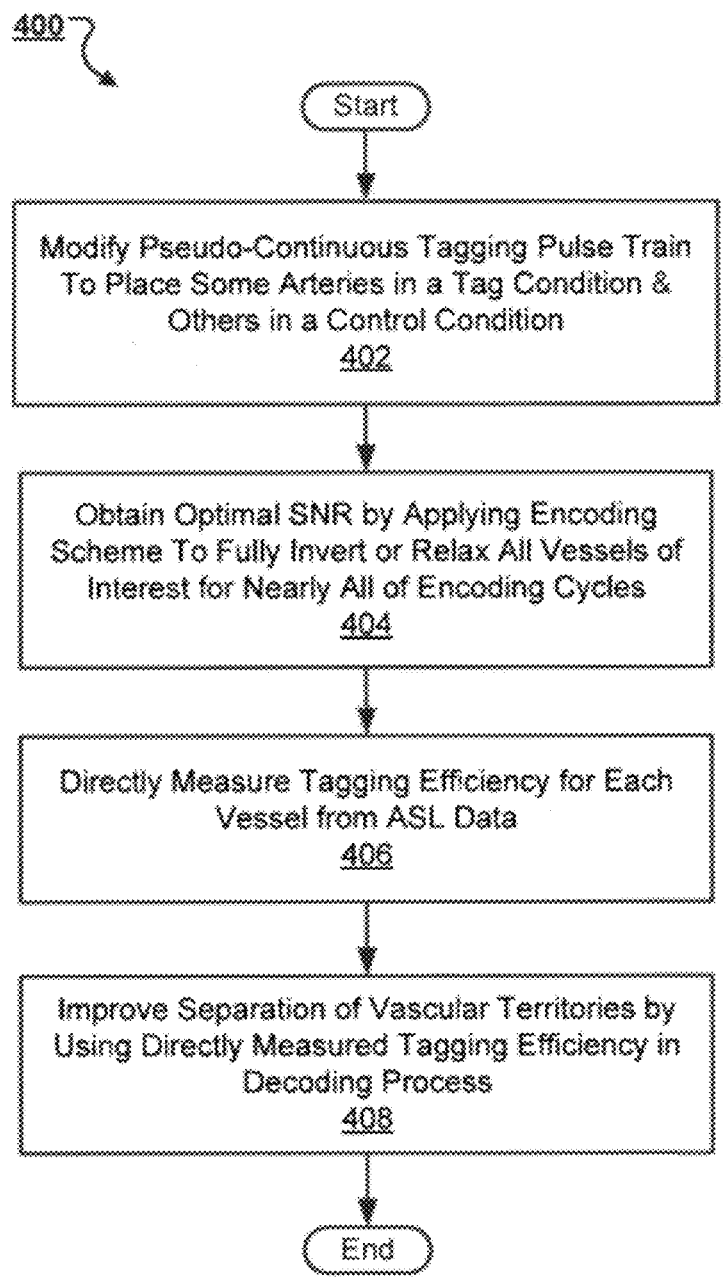
FIG. 4 shows an example process for SNR efficient mapping of vascular territories based on pseudo-continuous ASL.

Vessel Encoded Arterial Spin Labeling Using Pseudo-Continuous Tagging—Unipolar Vessel Encoding Lobes FIG. 4 shows an example process 100 for SNR efficient mapping of vascular territories based on pseudo-continuous ASL. A pseudo-continuous tagging pulse train is modified 402 using additional transverse gradient pulses and phase cycling to place some arteries in a tag condition and others passing through the same tagging plane in a control condition. This is combined with a Hadamard or similar encoding scheme such that all vessels of interest are fully inverted or relaxed for nearly all of the encoding cycles, providing 404 optimal SNR. The relative tagging efficiency for each vessel is measured 406 directly from the ASL data and is used in the decoding process to improve 408 the separation of vascular territories. High SNR maps of left carotid, right carotid, and basilar territories can be generated in 6 minutes of scan time, for example.

Vessel Encoding

In non-vessel encoded ASL, the scan consists of two image types. Both image types contain identical static tissue signal but differ in the sign of the inflowing arterial magnetization.

This encoding process can be described mathematically by y=Ax where x is the contribution to the signal from inflowing blood and static tissue components, A is the encoding matrix, and y is the resulting signal intensities as shown in Equation (1) below.

$$y = \begin{bmatrix} y_1 \\ y_2 \end{bmatrix} \quad \text{Equation [1]}$$

$$A = \begin{bmatrix} -1 & 1 \\ 1 & 1 \end{bmatrix}$$

$$x = \begin{bmatrix} V \\ S \end{bmatrix}$$

In Equation (1) above, V is the MR signal of inflowing blood and S is the MR signal of static tissue. The rows of A are the encoding steps necessary to generate $y_1$ and $y_2$, which are typically referred to as 'tag' and 'control' images. The ASL signal V can be recovered by subtraction of $y_2-y_1$. More formally, when A has a pseudo-inverse $A^+$, x can be reconstructed by inversion to yield $x=A^+y$ as shown in Equation (2) below.

$$\begin{bmatrix} V \\ S \end{bmatrix} = A^+ y = 0.5 * \begin{bmatrix} -1 & 1 \\ 1 & 1 \end{bmatrix} \begin{bmatrix} y_1 \\ y_2 \end{bmatrix}, \quad \text{Equation [2]}$$

Thus, the same result is obtained that V is proportional to $y_2-y_1$.

In order to separately encode the contribution of more than one vessel to the MR signal, more than two encoding steps may be necessary, in which the vessels of interest are encoded in different patterns. The three-vessel encoding scheme as described in Gunther (Gunther M. Efficient visualization of vascular territories in the human brain by cycled arterial spin labeling MRI. Magn Reson Med 2006; 56(3):671-675) is shown in Equation (3).

$$\begin{bmatrix} y_1 \\ y_2 \\ y_3 \\ y_4 \end{bmatrix} = \begin{bmatrix} -1 & 1 & -1 & 1 \\ 1 & -1 & -1 & 1 \\ -1 & -1 & 1 & 1 \\ 1 & 1 & 1 & 1 \end{bmatrix} \begin{bmatrix} R \\ L \\ B \\ S \end{bmatrix} \quad [3]$$

and thus $$\begin{bmatrix} R \\ L \\ B \\ S \end{bmatrix} = 0.25 * \begin{bmatrix} -1 & 1 & -1 & 1 \\ 1 & -1 & -1 & 1 \\ -1 & -1 & 1 & 1 \\ 1 & 1 & 1 & 1 \end{bmatrix} \begin{bmatrix} y_1 \\ y_2 \\ y_3 \\ y_4 \end{bmatrix},$$

where R, L, and B are the contributions of tagged blood signal from the right carotid, left carotid, and basilar arteries, respectively. In both of the above examples, the encoding matrix consists of columns from a Hadamard matrix (Paley REAC. On Orthogonal Matrices. Journal of Mathematics and Physics 1933; 12:311-320). The resultant encoding is SNR optimal in the sense that all inflowing blood is either fully inverted or fully relaxed for each tagging cycle, and there are equal numbers of tag and control conditions for each vessel. All encoding matrices that consist of columns from a Hadamard matrix will have these properties, even if they are not square, and decoding of this type of data amounts to simple subtraction of the tag from control images for each vessel. In general, vessel geometry and tagging methodology may not allow for optimal encoding, but the expected SNR efficiency can be calculated from the decoding matrix $A^+$. For unit signal and unit noise, the decoding process outlined above will produce unit signal, because it is a direct inversion of the encoding process, while the noise for each territory will be given by the square root of the sum of squared elements across a row of $A^+$. For comparison, the SNR for simple averaging across N samples with unit signal and noise per sample is $\sqrt{N}$. A ratio of these SNR values can be represented as an index E of SNR efficiency as shown in Equation (4).

$$E_i = \frac{SNR_{encoded}}{SNR_{averaging}} = \frac{1 / \sqrt{\sum_j A_{i,j}^{+2}}}{\sqrt{N}} = \frac{1}{\sqrt{N \sum_j A_{i,j}^{+2}}}, \quad \text{Equation [4]}$$

where N is the number of samples (and therefore the number of columns in $A^+$). For any Hadamard encoding scheme, E=1.

Tagging Method

The modulation of tag and control states can be accomplished using either pulsed or continuous ASL methodology. In this specification, the focus is on one or more modifications of the pseudo-continuous ASL (PCASL) tagging technique (Garcia DM, de Bazelaire C, Alsop D. Pseudo-continuous flow driven adiabatic inversion for arterial spin labeling. Proceedings of the International Society for Magnetic Resonance in Medicine; 2005; Miami. p 37) that provides efficient modulation of tag and control states across vessels within a single tagging plane.

In PCASL, a train of closely spaced RF pulses, in conjunction with a synchronously pulsed gradient field, effects a flow driven adiabatic inversion as blood flows through the tagging plane. Requirements for both the mean gradient and the mean RF amplitude to satisfy adiabatic conditions are similar to those of continuous ASL, and the mechanism of tagging is identical. Because the RF is applied in the presence of a larger gradient than in continuous ASL, the RF irradiation is farther off resonance in the target tissue, and magnetization transfer effects are greatly reduced. In PCASL, additional transverse gradient pulses can be applied during the time gaps in between the RF pulses to modulate the relative phase of spins in different vessels within the tagging plane.

The PCASL technique is modified to enable differential encoding of vessels within the inversion plane. In one modification, a single labeling gradient waveform is applied in the direction of flow with non-zero mean for both tag and control conditions. In another modification, additional gradients are applied perpendicular to the labeling gradient to generate phase shifts between the vessels of interest. In yet another modification, RF phase modulation is applied across pulses to place the vessels of interest in tag and control conditions according to the encoding schedule. These modifications can be defined as vessel encoded pseudo-continuous ASL (VEP-CASL) techniques where two or more vessels flowing through the tagging plane are differentially tagged and encoded across image repetitions.

Figure 5A:
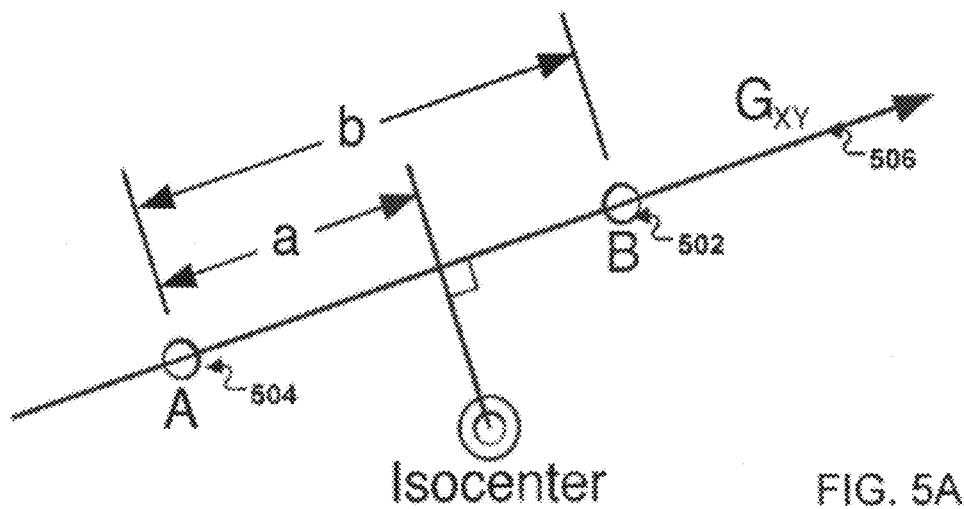
FIG. 5A shows an example of a diagram of tagging geometry for two vessels A and B, separated by distance b.
Figure 5B:
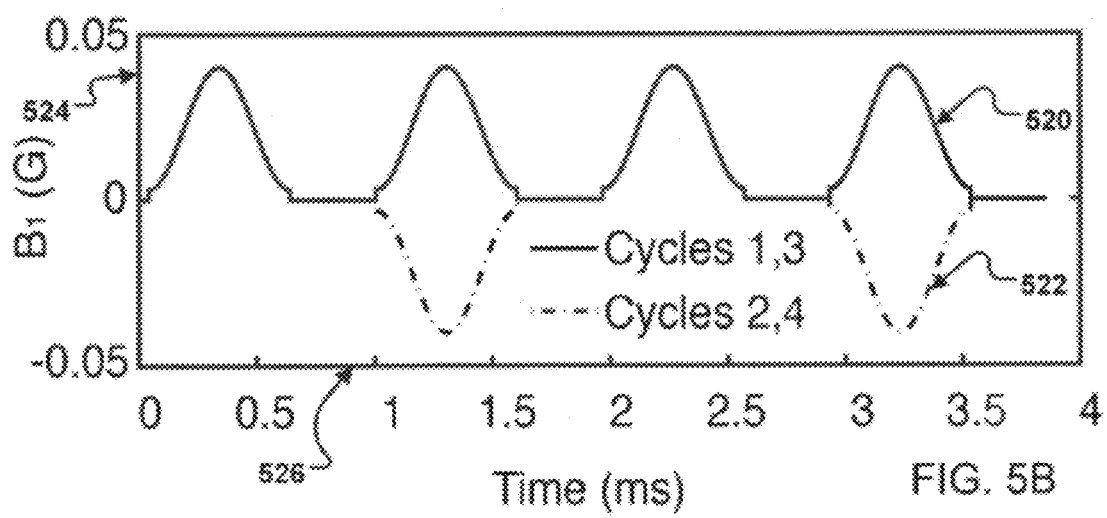
FIG. 5B shows an example of RF waveforms for a small segment of the tagging pulse train.
Figure 5C:
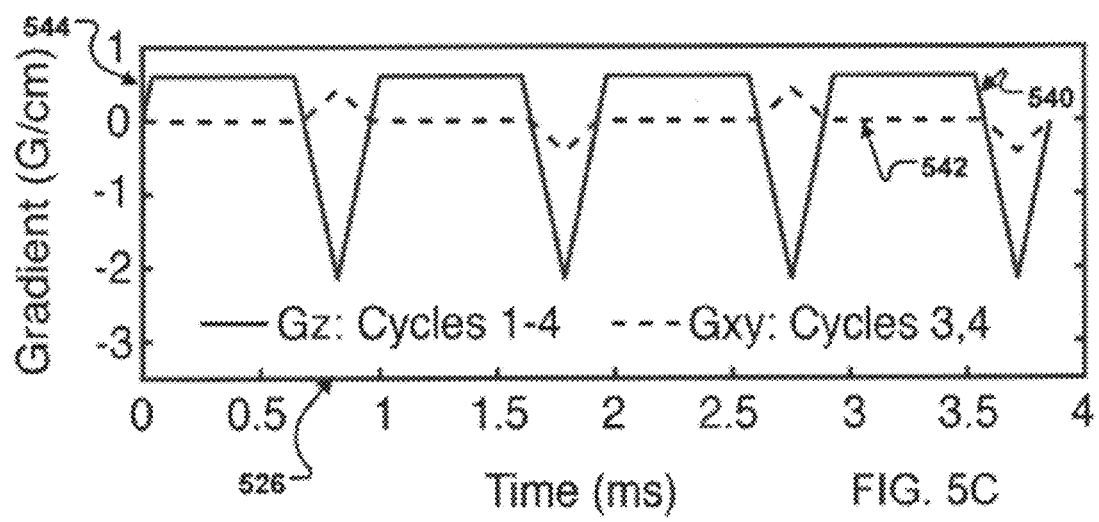
FIG. 5C shows an example of gradient waveforms for a small segment of the tagging pulse train for four cycles.

FIGS. 5A, 5B and 5C show examples of a tagging geometry and a pulse train for four cycles. FIG. 5A shows an example of a diagram of tagging geometry for two vessels A and B (504, 502), separated by distance b. Within the tagging plane, $G_{xy}$ 506 is applied along the line from one vessel to the other, and vessel A 504 is a distance from the projection of the isocenter onto this line.

FIG. 5B shows an example of RF waveforms 520, 522 for a small segment of the tagging pulse train. The waveforms 520, 522 are plotted with vertical axis 524 representing waveform amplitude and horizontal axis 526 representing time in milliseconds.

FIG. 5C shows an example of gradient waveforms 540, 542 for a small segment of the tagging pulse train, plotted with Gradient values on the vertical axis 544. Cycle 1 represents having all vessels inverted. Cycle 2 represent having no vessels inverted. Cycle 3 represents having only vessel A inverted. Cycle 4 represents having only vessel B inverted. In non-modified pseudo-continuous ASL, the labeling gradient ($G_z$) has non-zero mean for the tag condition and zero mean for the control condition. While it is sensible to use a gradient with zero mean for the control condition, this is not necessary in order to obtain a transparent control pulse (see RF pulse simulations below). For all four cycles the same tagging gradient in the direction of flow is used. For cycles 3 and 4, an additional gradient pulse ($G_{xy}$) is applied between RF pulses in the direction of the vector from one vessel to the other within the tagging plane. This pulse is applied with alternating sign and an area of $\pi/\gamma b$, where b is the separation between vessels, producing a phase shift of $\pi$ between the two vessels. If the phases of the RF pulses are adjusted so that all pulses are coherent with spins at the location of one vessel, then spins in that vessel experience adiabatic inversion, while spins in the other vessel experience pulses with alternating sign, resulting in a transparent pulse. The phase modulation across the RF pulse train for the 4 cycles is summarized as:

Cycle 1: $\phi_i = \phi_z$

Cycle 2: $\phi_i = \phi_z + (i \bmod 2)\pi$

Cycle 3: $\phi_i = \phi_z + \phi_{xyA}$

Cycle 4: $\phi_i = \phi_z + \phi_{xyB}$ $$\phi_z = i\gamma \overline{G}_z tz \quad \phi_{xyA} = (i \bmod 2)\pi(a/b) \phi_{xyB} = (i \bmod 2)\pi((b-a)/b) \quad [5]$$

where i is the pulse number, $\overline{G}_z$ is the mean value of $G_z$, t is the RF pulse spacing, z is the offset of the labeling plane from isocenter, 'mod' is the integer modulus function, and a and b are the vessel location and separation as shown in FIGS. 5A-C. The variable $\phi_z$ is the phase needed to keep the pulses coherent with spins under the influence of $G_z$, while $\phi_{xyA}$ and $\phi_{xyB}$ are the additional phases needed to keep the pulses in phase with spins in vessels 1 and 2, respectively, in the presence of $G_{xy}$. This encoding method generates alternating lines of tag and control conditions within the tagging plane.

Tagging Pulse Train Simulations

The effect of the mean gradient phase alternation, flow velocity, and resonance offset can be calculated by Bloch equation simulation for the following pulse train parameters: Hanning shaped RF pulses of 600 s duration and 0.04 G amplitude; gradient amplitude of 0.6 G/cm during RF pulses, with refocusing lobes applied at a slew rate of 15 G/cm/ms and a maximum magnitude of 4 G/cm. The flip angle at the center of the pulse profile is 20°, and the width over which the flip angle exceeds 2° is 2.0 cm. For the simulations, $T_2$ can be assumed to be 200 ms, and $T_1$ relaxation can be neglected in order to simplify the calculation of the tagging efficiency.

Imaging Parameters

Imaging is performed on a General Electric (Waukesha, Wis.) 3T scanner using a commercial 8-channel head RF coil array and the body coil for RF transmission, for example. The volunteers to be included in the scan group can include both male and female individuals of a predetermined age range. For example, four normal volunteers, two male and two female, of ages 25-45 were included in the scan group. The volunteers are scanned with prior informed consent under an IRB approved protocol. The FOV is determined to be 24 cm×8 mm with a 2 mm gap between slices, and single-shot 2D spiral readout is used. Tagging parameters include those described in the simulations above, with a total length of 1574 ms for the tagging pulse train, composed of 1640 RF pulses with a spacing of 960 s. Two non-selective adiabatic inversion pulses are applied 950 ms and 300 ms prior to image acquisition for background suppression. The post labeling delay is 1000 ms and TR was 3000 ms. Twenty images are acquired for each cycle of the encoding scheme, resulting in a scan time of 4 minutes for 2-vessel encoding, and 6 or 8 minutes for 3-vessel encoding. Mean and RMS B1 are 0.014 G and 0.020 G, respectively, during the tagging pulse train and the average whole body SAR reported by the integrated RF power monitor in the scanner was 1.7-1.8 W/Kg.

Data Processing

Vascular territory maps can be generated by pseudo-inversion of the encoding matrix as described above. Ideally, each vessel of interest is fully inverted or fully relaxed during each tagging period. In practice, because of vessel geometries and velocity distributions, this may not be always possible. In order to correct for this, the tagging efficiencies of the vessel encoded scans can be measured relative to non-selective scans and included in the encoding matrix. From the non-selective scan cycles of the encoding process (all vessels relaxed or all vessels inverted), a conventional ASL image can be calculated by simple subtraction. A signal intensity threshold is set, for example, at half of the intensity at the 99th percentile in this image, and voxels above this threshold is identified as a rough gray matter mask. Within this mask, the ratio of signal intensities for vessel encoded scans divided by non-selective scans is calculated on a voxel-wise basis and displayed as histograms. Local peaks in these histograms are fitted to Gaussian functions by least squares fitting to provide estimates of the tagging efficiency of each tagged vessel, relative to the tagging efficiency of the non-vessel encoded scan. These relative tagging efficiencies are referred to as β, and can be applied directly in the construction of the encoding matrices. No spatial smoothing or masking of signal outside the brain is applied, and images are displayed according to radiological convention (left of image is right of subject).

Figure 6C:
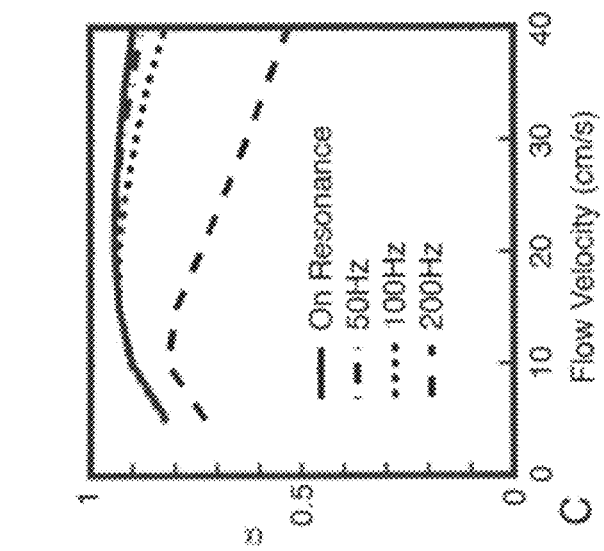
FIGS. 6A, 6B and 6C show examples of Bloch equation simulations of several features of a vessel encoding pulse train as shown in FIGS. 5B and 5C.
Figure 6B:
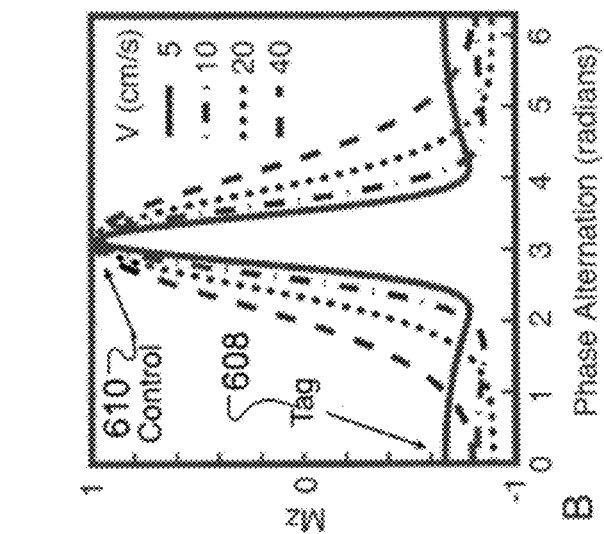
Figure 6A:
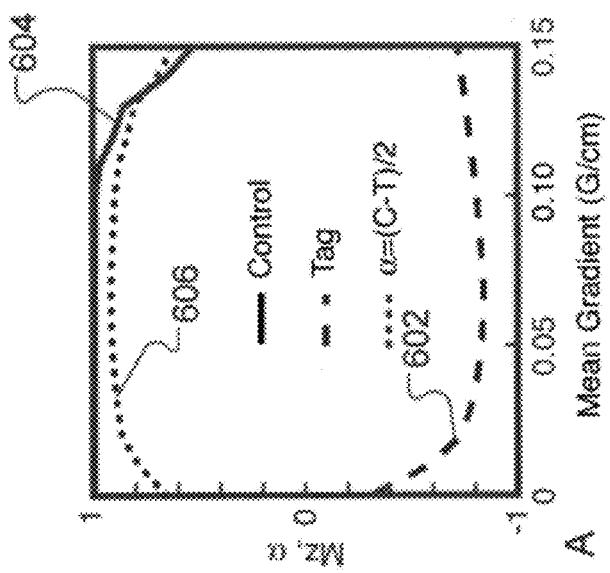

FIGS. 6A, 6B and 6C show examples of Bloch equation simulations of several features of a vessel encoding pulse train as shown in FIGS. 5A-C. FIG. 6A shows the calculated $M_z$ of spins of blood that have flowed through the tagging plane as a function of the mean tagging gradient $\overline{G}_z$, averaging across velocities from 5-40 cm/s. In the control condition 604 with RF alternation, the pulse train is transparent for $\overline{G}_z \leq 0.1$ G/cm. In other words, with a phase alternation of π between RF pulses, the perturbation of flowing spins is minimal for $\overline{G}_z$ from 0-0.1 G/cm, producing an efficient control condition across this range of mean gradients. In the absence of phase modulation (the tag condition) 602, efficient flow driven inversion occurs from approximately 0.04-0.12 G/cm, and the tagging efficiency 606 $\alpha = (M_{z,control} - M_{z,tag})/2$ has a broad peak centered at approximately $\overline{G}_z = 0.08$ G/cm. This value of $\overline{G}_z$ is used throughout in this specification.

FIG. 6B shows an example of a calculated response of $M_z$ as a function of RF phase alternation for a range of flow velocities. At locations between the two vessels of interest, intermediate values of $M_z$ are obtained. A vessel in the tag condition 602 experiences zero phase alternation 608, while one in the control condition experiences an alternation of π radians 610 from pulse to pulse. In the control condition, a phase shift of π radians per pulse is applied to make the pulse train transparent. Vessels in other locations experience intermediate levels of phase alternation according to their position along $G_{xy}$. From these curves one can calculate the expected tagging efficiency as a function of vessel position and velocity.

FIG. 6C shows the sensitivity of this tagging scheme to resonance offset. The tagging efficiency vs. resonance offset is calculated. Above 100 Hz resonance offset, a marked reduction of tagging efficiency is shown.

FIGS. 7A, 7B and 7C show examples of vessel encoded images from one subject. In FIG. 7A, rows A, B, and C show the results of three different two-vessel encoding schemes, with the encoding locations shown in FIG. 7C. In row A, the left and right carotid arteries are encoded and separable with high efficiency, but the posterior circulation cannot be clearly separated from the anterior circulation. In this subject, the right vertebral artery is dominant, and the posterior territory appears in the histogram as a peak with β≈−0.5 (see while arrows 402, 404, 406). In row B, the anterior and posterior circulations are separated using anterior/posterior encoding, while in row C, the same separation is accomplished using left/right encoding, but with lower measured β for all vessels. Row D shows a three vessel separation based on the data from rows A and B.

FIG. 7B shows example histograms of the measured tagging efficiencies for each encoding scheme. With perfect tagging efficiency the encoding and decoding matrices and SNR efficiency for this separation can be calculated as shown in Equation (6).

$$A = \begin{bmatrix} -1 & -1 & -1 & 1 \\ 1 & 1 & 1 & 1 \\ -1 & 0 & 1 & 1 \\ 1 & 0 & -1 & 1 \\ 1 & -1 & 1 & 1 \\ -1 & 1 & -1 & 1 \end{bmatrix} \quad [6]$$

$$A^+ = \begin{bmatrix} -.125 & 0.125 & -0.25 & 0.25 & 0.125 & -0.125 \\ -0.25 & 0.25 & 0 & 0 & -0.25 & 0.25 \\ -0.125 & 0.125 & 0.25 & -0.25 & 0.125 & -0.125 \\ 0.167 & 0.167 & 0.167 & 0.167 & 0.167 & 0.167 \end{bmatrix}$$

$$E = \begin{bmatrix} 0.943 \\ 0.817 \\ 0.943 \\ 1 \end{bmatrix},$$

where the columns of A correspond to the right carotid, basilar, left carotid, and static tissue components, respectively, and the rows represent 6 encoding cycles. The theoretical SNR efficiency is not 1 because 2 of the 6 encoding cycles generate zero signals from the basilar artery. Using the values of β measured from the histograms shown in FIG. 7B, Equation (6) can be rewritten as shown in Equation (7).

$$A = \begin{bmatrix} -1 & -1 & -1 & 1 \\ 1 & 1 & 1 & 1 \\ -0.99 & 0.50 & 1.04 & 1 \\ 0.99 & -0.50 & -1.04 & 1 \\ 1.01 & -0.71 & 1.01 & 1 \\ -1.01 & 0.71 & -1.01 & 1 \end{bmatrix} \quad [7]$$

$$A^+ = \begin{bmatrix} -.179 & 0.179 & -0.247 & 0.247 & 0.078 & -0.078 \\ -0.293 & 0.293 & 0 & 0 & -0.291 & 0.291 \\ -0.029 & 0.029 & 0.247 & -0.247 & 0.214 & -0.214 \\ 0.167 & 0.167 & 0.167 & 0.167 & 0.167 & 0.167 \end{bmatrix}$$

$$E = \begin{bmatrix} 0.918 \\ 0.700 \\ 0.880 \\ 1 \end{bmatrix}.$$

Across four subjects, the average value of β is 0.94±0.07 in the carotid arteries, and across three subjects 0.69±0.14 in the vertebral arteries.

Figures 8A, 8B:
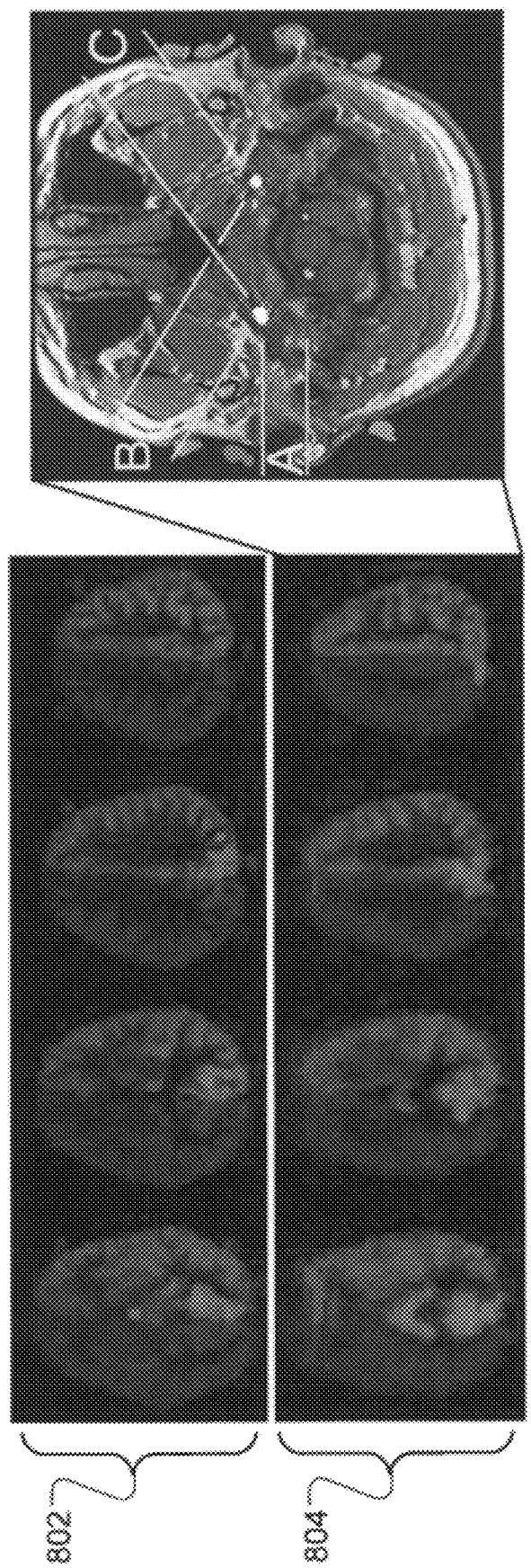
FIGS. 8A and 8B show examples of three vessel encoding from two additional subjects.

FIGS. 8A and 8B show examples of three vessel encoding from two additional subjects. In the top row 802, the encoding method is identical to that used for FIG. 7A, row D, but in this subject, the basilar circulation supplied only the left posterior cerebral territory, which was consistent with MR angiographic findings. In addition, the right anterior cerebral territory appears to be supplied by mixed left and right carotid blood suggesting active flow in the anterior communicating artery. In the lower row 804, an 8 cycle Hadamard scheme is used to encode the vessels in the neck as shown in FIG. 8B. Each of the vessel encodings A, B, and C, as shown in FIG. 8B, contrast two vessels with the third. While the theoretical values of E for this encoding are [1, 1, 1, 1], the measured β ranged from 0.54-0.91, and the SNR efficiency is E=[0.88, 0.80, 0.89, 1].

Figures 9A, 9B:
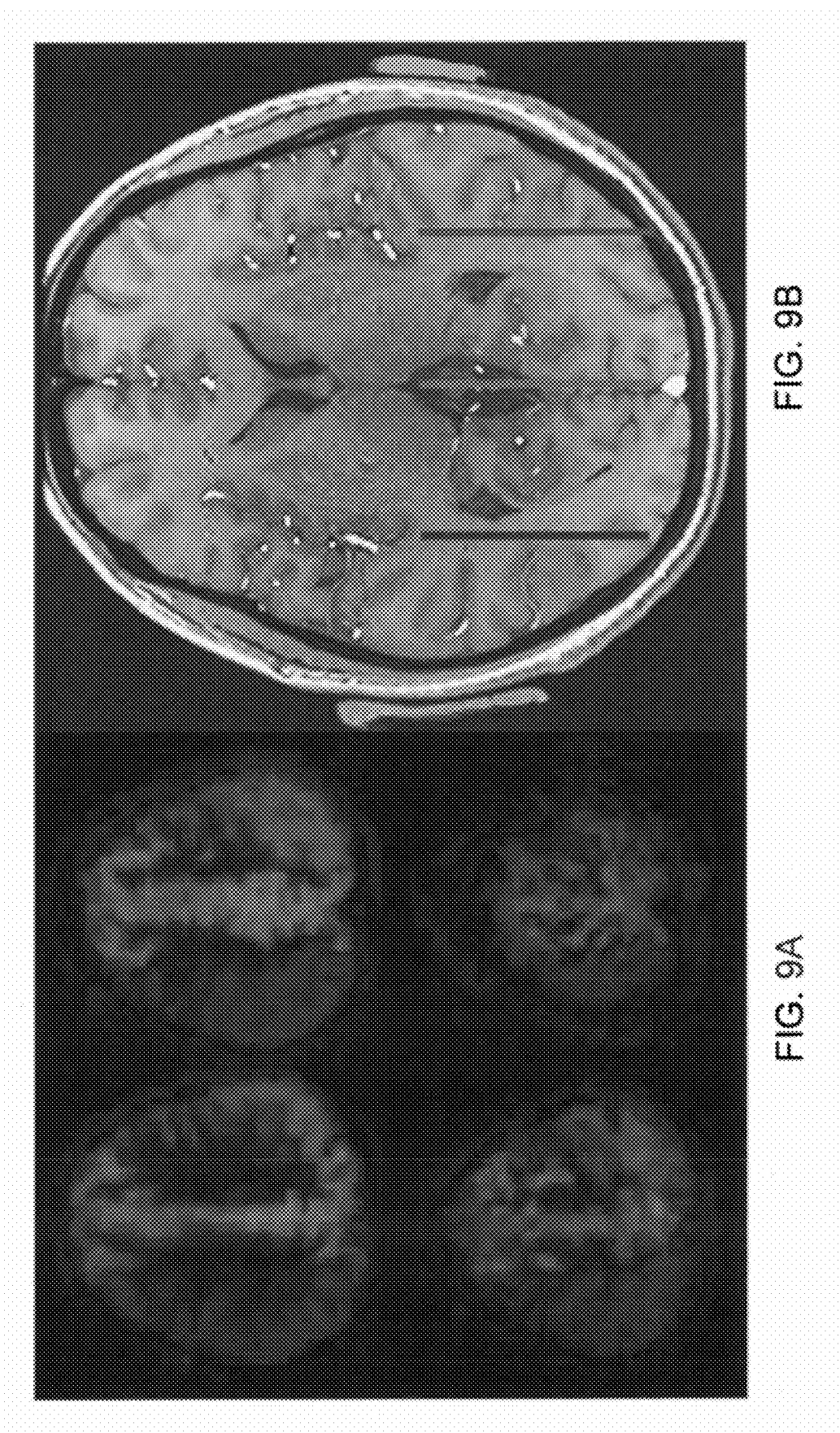
FIGS. 9A and 9B show an example of vessel encoding above the Circle of Willis.

FIGS. 9A and 9B show an example of vessel encoding above the Circle of Willis. In this example, three vascular territories, left middle cerebral artery (MCA), anterior cerebral artery (ACA), and right MCA, are mapped using left/right encoding, analogous to scans A and C in FIG. 7A. While the ACA and some branches of the MCA along the insula are tagged with high efficiency, there are other branches of the MCAs that are not well tagged, hence the incomplete representation of the anterior portion of the MCA territories. For left MCA, ACA, and right MCA, E=[0.85, 0.82, 0.85].

Figure 10:
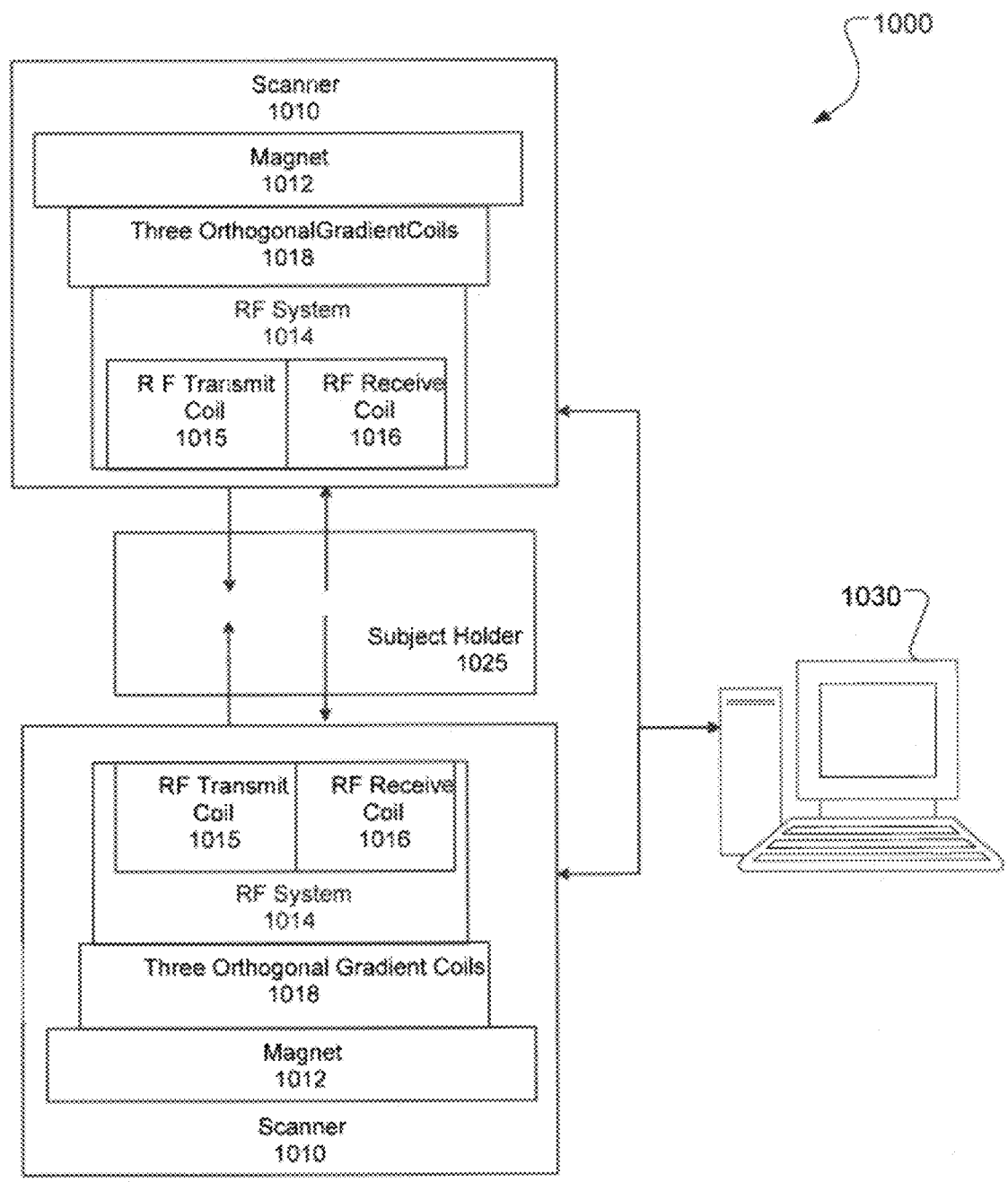
FIG. 10 shows an example of an MRI system.

FIG. 10 shows an example MRI system 1000. Techniques as disclosed in this specification can be implemented using the MRI system 1000. The MRI system 700 can be implemented using any one of various MRI scanners such as a 1.5 T Sigma TwinSpeed scanner (available from GE Healthcare Technologies, Milwaukee, Wis.) The MRI system 1000 includes a scanner 1010, a data processing apparatus 1030 and a subject holder or table 1025 for holding a subject 1020. The scanner 1010 includes a main magnet 1012, three orthogonal gradient coils 1018 and a RF system 1014. The main magnet 1012 is designed to provide a constant, homogeneous magnetic field. The three orthogonal gradient coils 1018 are designed to provide three orthogonal, controller magnetic gradients used to acquire image data of a desired slice by generating an encoded and slice-selective magnetic field. The RF system 1014 includes a RF transmit coil 1015 and a RF receive coil designed to transmit and receive RF pulses. The RF system 1045 can further include a RF synthesizer (not shown) and a power amplifier (not shown). In some implementations, an integrated transceiver coil (not shown) can be implemented instead of the separate transmit coil 1015 and receive coil 1016 for transmitting and receiving RF signals. For example, a close-fitting smaller coil can improve image quality when a small region is being imaged. Further, various types of coils that are placed around specific parts of a body (e.g., the head, knee, wrist, etc.) or even internally can be implemented depending on the sample and imaging applications.

The MRI system 1000 is designed to perform the techniques disclosed in this specification. In particular, the MRI system 1000 is designed to implement the methods disclosed with respect to FIG. 4. The RF system 1014 is designed to apply to a target subject 1020 a non-selective inversion RF pulse, a slice-selective inversion RF pulse and a half RF excitation pulse. The three orthogonal coils 1018 are designed to apply slice-selective magnetic field gradients (of a first polarity and a second polarity) and magnetic readout gradients. The data processing apparatus (e.g., a computer) 1030 is designed to receive and process the acquired data to obtain desired images corresponding to the short T2 components. For example, the data processing apparatus can perform the dual echo subtraction.

The vessel encoded PCASL techniques described in this specification provide simultaneous perfusion images of two or more vascular territories, with SNR that is close to that of conventional ASL images with the same total scan time. The data processing techniques described in this specification enable direct estimation and correction of the relative tagging efficiencies β associated with the vessel encoding process. Advantages of these techniques over the conventional pulsed methods include higher SNR of the pseudo-continuous tagging process and spatial specificity gained from encoding of vessels within a single tagging plane.

Discrimination between two vessels depends only on separation of the vessels as they pass through the tagging plane, rather than on the identification of three dimensional slabs that contain sufficiently long segments of one vessel or the other for pulsed tagging. In addition, the temporal width of the tag bolus is naturally identical for all tagged vessels, simplifying quantitation of perfusion. As in conventional continuous or pseudo-continuous ASL, the tagging process does not need to perturb spins either proximal or distal to the tagging plane, allowing for arterial spins proximal to the tagging plane to remain relaxed for the next tagging cycle, and for the tag to be placed close to the imaging region when this is desirable. While only those vessels located along parallel lines within the tagging plane may be tagged with full efficiency, this generally does not pose a problem for encoding of 3 vessels. For encoding of 4 or more vessels, the vessels may not fall along two parallel lines. In these cases, less efficient encoding may be accepted, or new tagging pulses developed to enable curved tagging lines.

Because the tagging pulses perturb spins over a range of approximately 2 cm, a tagging plane with arterial segments that are relatively straight over this distance should be used. The minimum distance between the tagging plane and the most proximal imaging location is limited by the slice profile of the tagging pulses, and by magnetization transfer effects to approximately 2 cm.

Quantitation of perfusion using the techniques described in this specification can be the same as that for non-selective PCASL. The relative tagging efficiencies β of the vessel encoded scans are measured and included in the decoding process, resulting in decoded images that are on the same absolute scale as non-vessel encoded PCASL images. The additional terms in the signal equations for PCASL, such as those that account for the basic tagging efficiency α, the tag duration, and relaxation are scaling terms that can be treated separately from the encoding/decoding process.

The identification of optimal tagging/encoding parameters and geometries, as well as efficient techniques for prescribing these geometries have been described. The efficient separation of the three main inputs to the Circle of Willis has also been shown in this specification using two different encoding schemes as described with respect to FIGS. 7A-8B. The optimization of the techniques as described in this specification may be dependent on the interaction between the tagging parameters, the vascular geometry and the velocity distributions. For example, slower flow velocities above the Circle of Willis may call for PCASL parameters that are better tuned for those velocities. Tagging in areas of greater vessel may be improved using pulses with narrower slice profile, in order to reduce the amount of in-plane flow as blood traverses the tagging plane.

In the VEPCASL techniques as described with respect to FIGS. 4-9B above, two or more vessels flowing through the tagging plane are differentially tagged and encoded across image repetitions. Hadamard type encoding and a linear model are used to estimate the contribution of each vessel to the perfusion of each voxel. For some tagging planes, such as above the Circle of Willis, many arteries pass through the tagging plane, and unique Hadamard encoding of each vessel can be difficult.

In some implementations, additional data processing techniques can be implemented to better extract information from multiple vascular territories. In particular, the continuous nature of the spatial modulation of tagging across the tagging plane in VEPCASL can be used to identify multiple vascular territories with a small number of encoding steps. Branches of the M2 Segment of the MCA can be mapped using at least two approaches.

In VEPCASL, the relative tagging efficiency β varies periodically and roughly sinusoidally across the tagging plane from +1 to −1. In one data processing technique, the measured tagging efficiencies can be mapped to vessel coordinates. In particular, two A/P encoded images S and C are collected with the tagging modulation shifted by one half cycle in the second image. The collected images generate arterial magnetization $M_{zS} \propto \sin(2\pi y/Y)$ and $M_{zC} \propto \cos(2\pi y/Y)$, where Y is the spatial period of the modulation. At each voxel, the ASL signal is related to the location y of the source vessel by y=Y arctan (S/C)/$2\pi$, and the y position of the vascular source can therefore be localized modulo Y.

In another data processing technique, the tagging efficiencies can be measured from the data by clustering. Two or more vessel encoded images are acquired, and the relative tagging efficiency β is calculated for each voxel. For N vessel encoded images, β can be represented as a point in N dimensional space, and voxels with a common vascular source will cluster in that space. Conventional cluster analysis can then be used to identify clusters in β, and the centroid of each cluster can be used to estimate the position of the source vessel.

To obtain data, Volunteer subjects are scanned under IRB approval using the MRI system 1000 such as the 3T GE scanner (from General Electric). Using the MRI system 1000, images are acquired using single shot spiral imaging at 64×64 matrix, 20 cm FOV with 6 mm slices. Vessel encoding is performed as described with respect to FIGS. 4-9B above. The resultant images are shown in FIGS. 11-15. Total scan time is 8 min for FIGS. 11-13 and 12 min for FIGS. 14-15.

Figure 11:
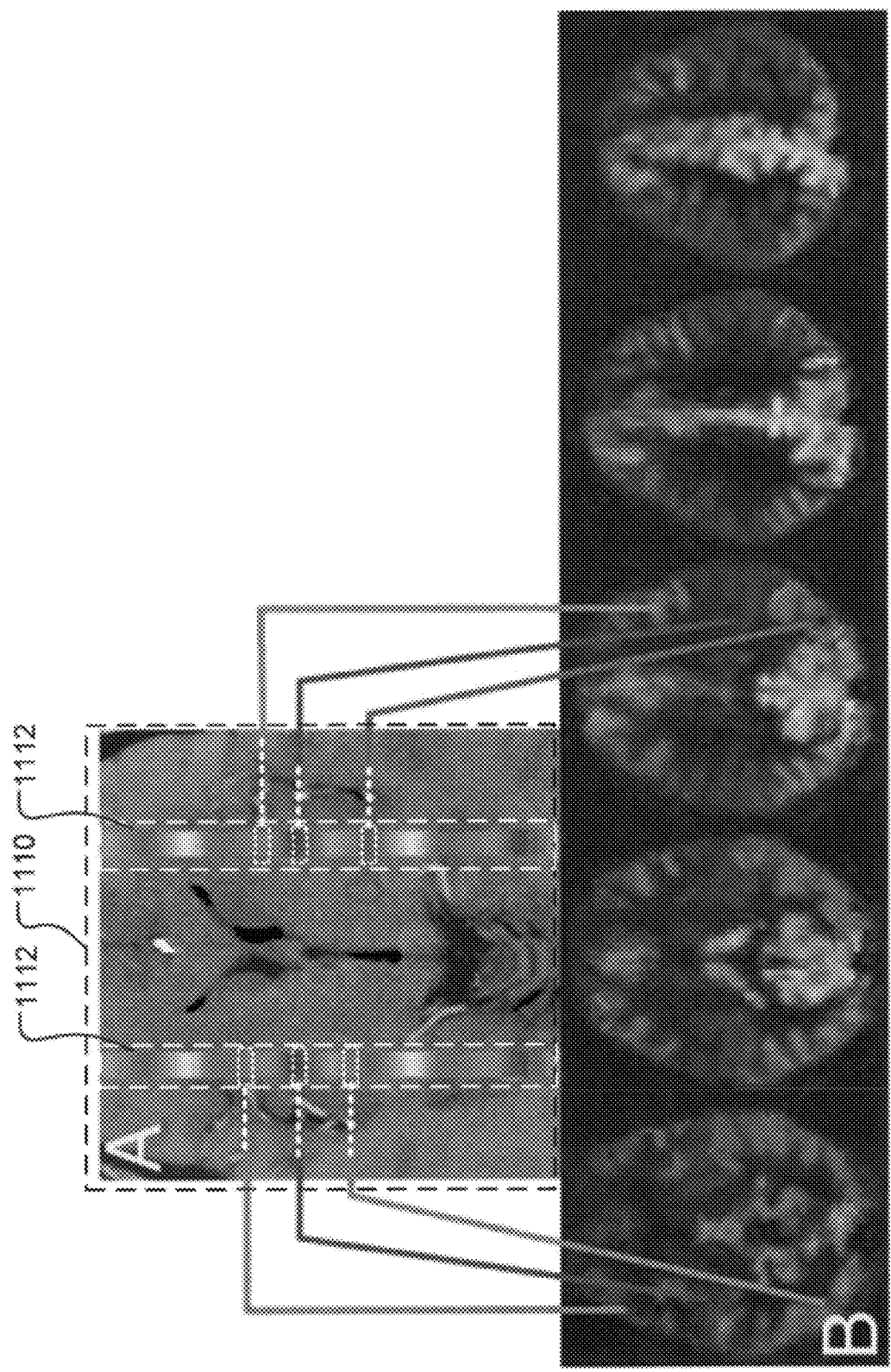
FIG. 11 shows examples of sine (sin)/cosine (cos) modulations.

FIG. 11 shows example sine (sin)/cosine (cos) modulations. For the example shown in FIG. 11, amplitude/phase (A/P) modulation of the tagging can be performed with Y=54 mm. The top image 1110 represents a tagging plane. In the tagging plane, a color/shaded scale 1112 is included to show the predicted phase angle arctan(S/C).

The bottom image 1120 has pixel intensity proportional to the absolute ASL signal, but is colorized or shaded according to arctan(S/C), on the color or shade scale 1112. For each vascular territory, the y position of the vascular source can be identified by color/shade. On both sides of the brain, three branches of the M2 segment of the MCA can be identified on both the angiogram and the vascular territory maps.

Figure 12:
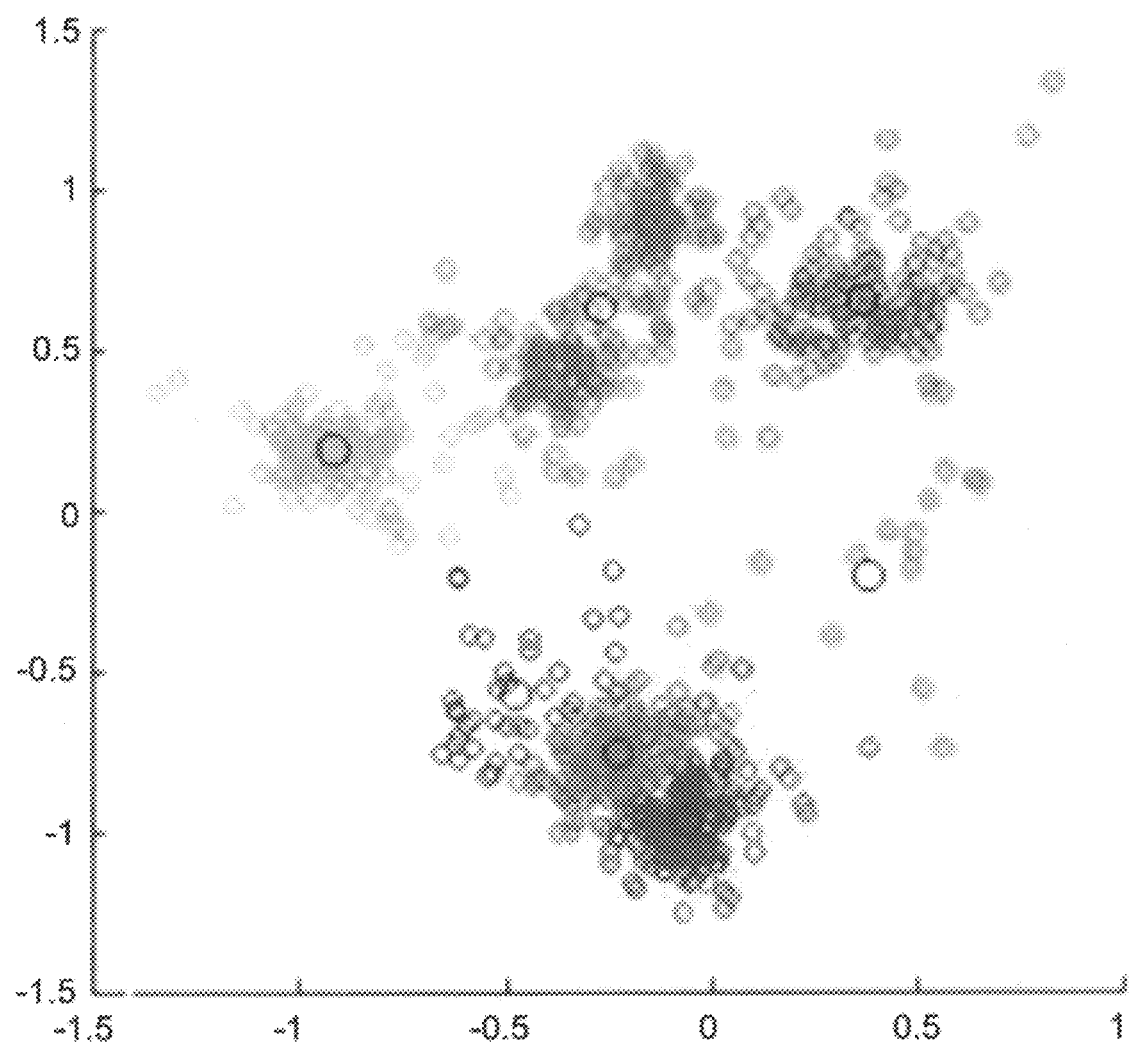
FIGS. 12, 13, 14 and 15 show example clustering techniques.
Figure 13:
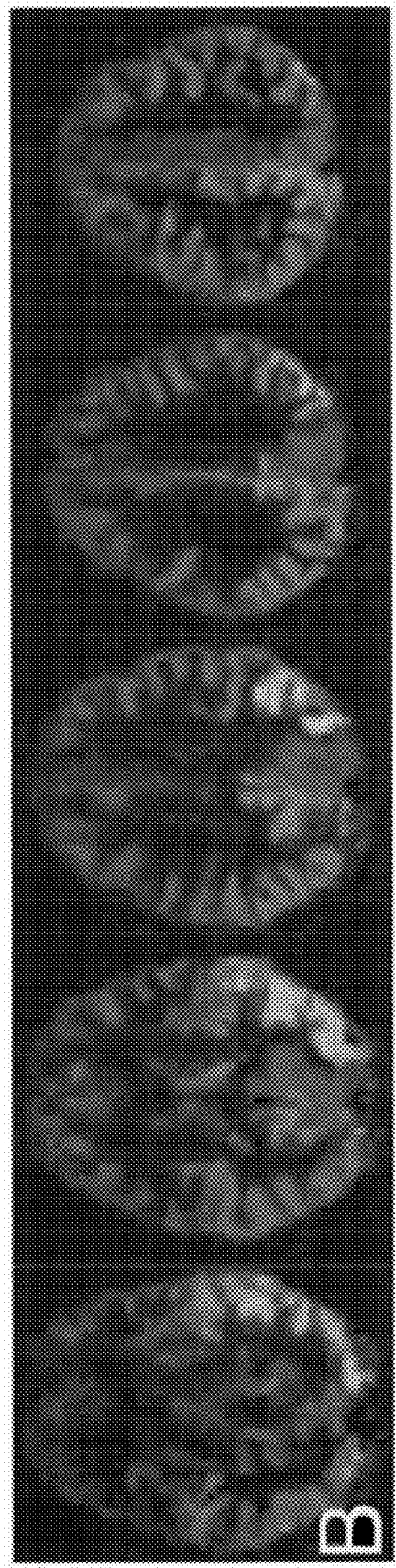

FIGS. 12-15 show example clustering techniques. Using the same data shown in FIG. 11, the clusters in two dimensional R space are shown in FIG. 12. Clusters are identified automatically using an Expectation Maximization Gaussian Mixture clustering routine in MATLAB, for example. Clusters are colorized or shaded with the same colors or shades of the corresponding voxels in FIG. 13. These techniques enable identification of the posterior branch of the MCA on the left and right sides as being different based only on slight differences in the A/P location of the arteries.

Figure 14:
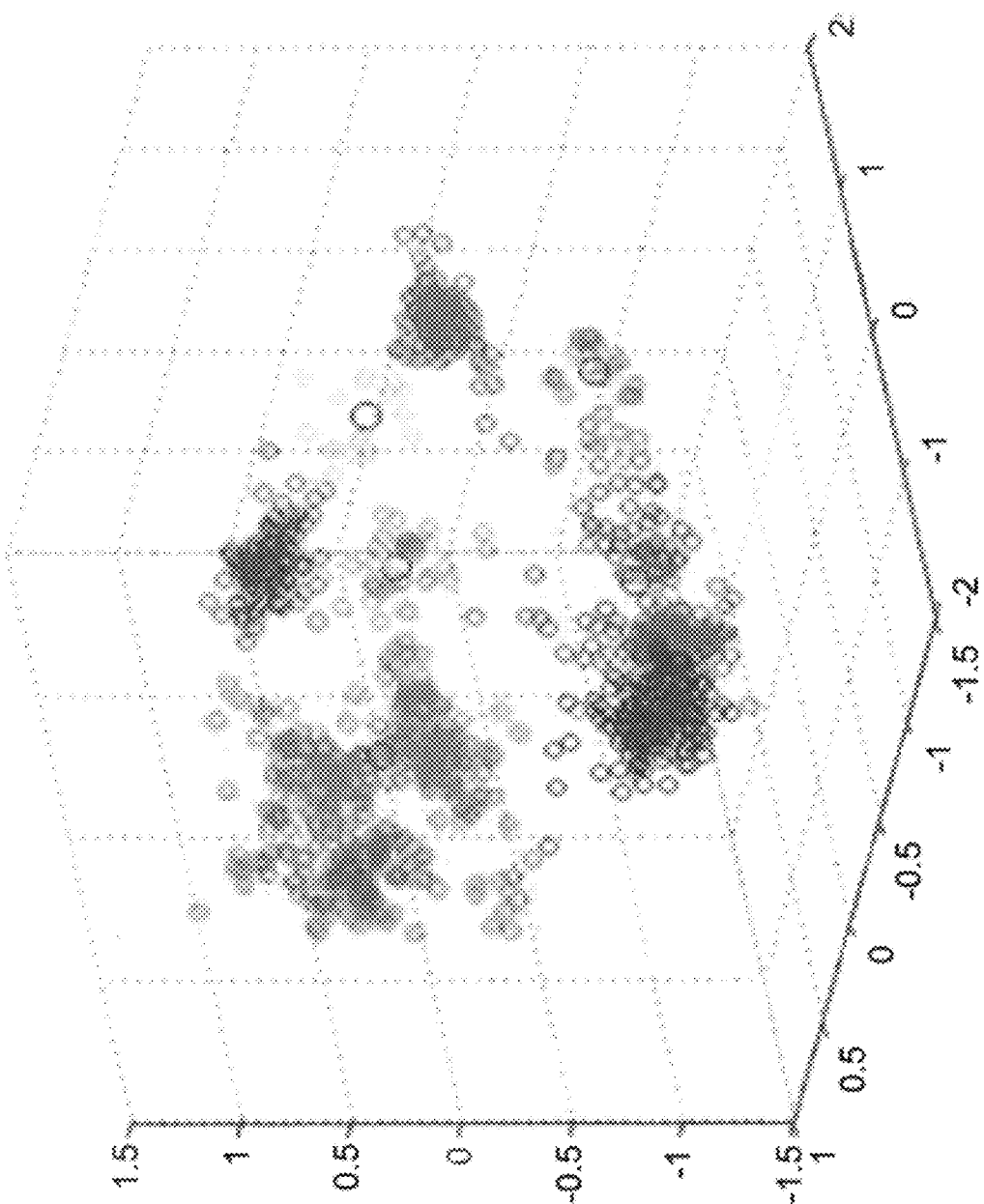
Figure 15:
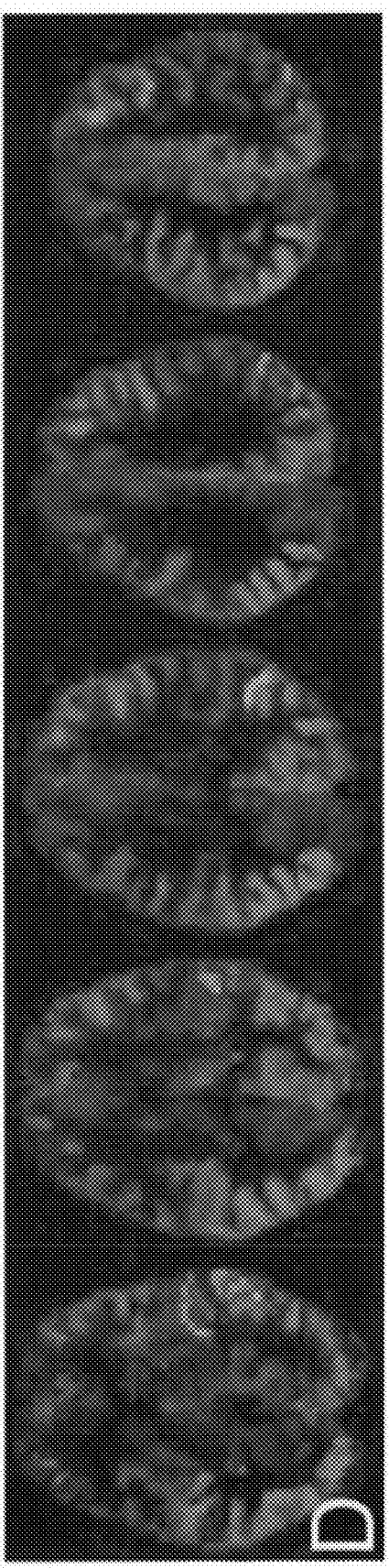

The clusters in FIG. 12 are expected to fall along a circle. However, inefficiencies in tagging due to variations in vessel curvature, flow velocities, $B_1$, and $B_0$ can cause the clusters to not fall along a circle. The phase angle in FIG. 12 is the azimuthal angle in FIG. 13. For FIGS. 14 and 15, a third data set containing L/R encoding is added to provide a clean separation between left and right source vessels. The β space and clustering are 3 dimensional, and the clusters are shown in FIG. 14. While left/right encoding is not itself of use in this case, an additional axis can separate clusters that may otherwise partially overlap, and thereby improve the accuracy of the localization of the cluster centroids.

Because VEPCASL provides a graded modulation of tagging efficiency across space, several vascular territories can be identified using a small number of encodings, limited only by the SNR of the measurement of β. At least 3 branches of each MCA can be separated at the M2 segment. The advantage of the sin/cos encoding method is that it does not depend on data fitting or clustering, and is fast and robust. The clustering based method allows for the inclusion of multiple dimensions of encoded data, which generally improves the separation of clusters. However, fully automated detection of clusters is not always robust.

Implementation Examples

With respect to FIGS. 16 to 20, results for blind detection of vascular sources and territories using random vessel encoding arterial spin labeling, obtained in some lab and medical experiments are now described. In one aspect, these results show the effectiveness of the disclosed techniques to use vessel encoded arterial spin labeling (VEASL) methods to detect feeding arteries without prior knowledge of their positions, and map the vascular territory of each.

Materials and Methods

Five healthy subjects were scanned, each with four different tagging planes. The VEASL tagging method was modified to use 60 different pairs of encoding steps with random orientation and spacing. A signal model was developed to calculate the theoretical ASL signal resulting from a vessel in any position in the tagging plane. For each voxel, the location of the feeding vessel was estimated by finding the theoretical signal that correlates most closely with the data.

Results in Brief

The main intracranial arteries, including carotid, vertebral, basilar, and cerebral arteries above the Circle of Willis were identified and localized from the ASL data in all subjects. In addition, external carotid branches were detected in all subjects.

Conclusions in Brief

Randomly encoded VEASL provides data that allows for blind detection of source vessels. This method simplifies the VEASL prescription process and allows for efficient detection of atypical or collateral circulation.

Introduction of the Experimental Setup

For most ASL methods, one goal is to provide accurate and robust measures of perfusion. However, through manipulation of the tagging process, ASL can be extended to provide additional information on which source vessels supply which target tissues. This information, which is typically in the form of vascular territory maps, may be useful for applications such as the evaluation of stroke, risk assessment in cerebrovascular disease, and planning of treatment for tumors. ASL-based territory mapping methods include some which apply ASL tags to single vessels, and others which encode the tagging process for two or more feeding arteries such that multiple vascular territories can be decoded and mapped simultaneously. One of these methods is vessel encoded arterial spin labeling (VEASL), in which pseudo-continuous ASL (PCASL) tagging is used with additional gradient pulses applied across the tagging plane to encode the ASL data with information about the location of the feeding arteries. In present art, VEASL requires prior knowledge of the locations of vessels to be tagged in order to prescribe a series of Hadamard encoding steps across the source vessels. This in turn necessitates the collection of an angiogram, and user input or an automated algorithm for detection of vessel locations in the tagging plane. In an effort to automate the scan prescription process, a planning-free VEASL method was recently introduced that uses a small number of generically defined encoding steps, and demonstrated repeatable detection of flow territories using this approach.

The present document discloses the use of a large number of random (non-uniform or uncorrelated) encoding steps to not only map vascular territories without planning, but to also uniquely identify the locations of the source arteries in the tagging plane. This provides the opportunity to identify collateral or atypical routes of circulation that may not previously be known, and may be clinically relevant.

In addition to the positions of feeding arteries, resonance offsets at the locations of the arteries in the tagging plane can also significantly affect the tagging efficiency, and methods have been proposed to either measure and correct for these offsets or to reduce sensitivity to them using multiphase PCASL. The randomly encoded method disclosed in this document allows for efficient estimation of both the locations and resonance offsets of feeding arteries without prior knowledge of either. Portions of this work were presented in abstract form in.

Materials and Methods

Figure 16:
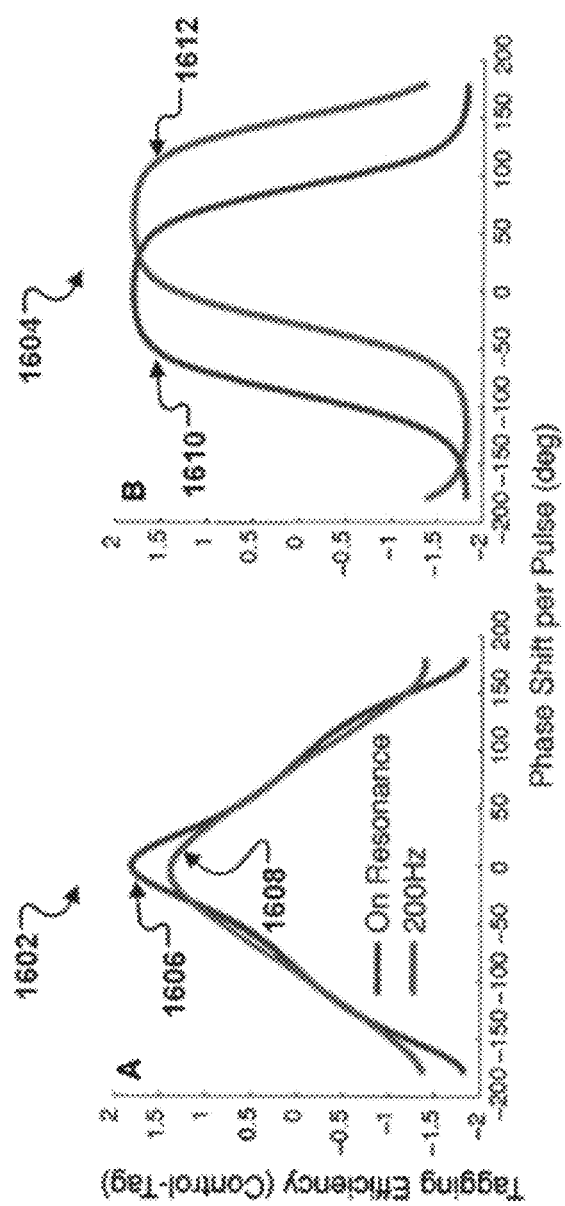
FIG. 16 depicts calculated VEASL signal as a function of transverse gradient induced phase shift per pulse, including Bipolar gradient pulses and Unipolar pulses. A resonance offset at the tagging location results in reduced tagging efficiency for the bipolar pulse train, but a simple shift without amplitude reduction for the unipolar pulse train.
Figure 17:
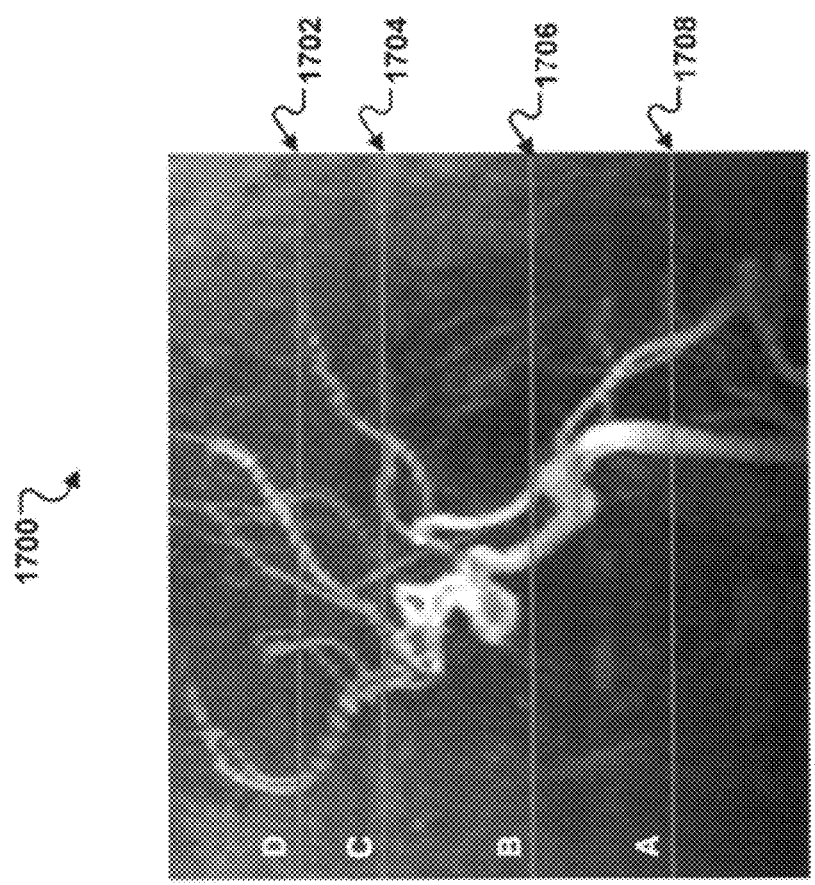
FIG. 17 depicts an example MR angiogram with tagging planes superimposed on a sagittal projection of the MR angiogram. (A) Trapezoidal arrangement of internal carotid and vertebral arteries; (B) Triangular arrangement of internal carotid and basilar arteries at the level of the sphenoid sinus; (C) and (D) Above the Circle of Willis, allowing tagging of anterior and posterior cerebral arteries, and branches of the middle cerebral artery.

In the currently practiced VEASL, transverse gradient pulses of alternating sign are used between RF pulses to provide vessel encoding (graph 1602). In the presence of resonance offsets in the tagging plane, this approach results in decreased tagging efficiency, as shown in FIG. 16. These curves 1606, 1608, 1610, 1612 were calculated by Bloch simulation, assuming a range of flow velocities uniformly distributed from 5 to 40 cm/s in the direction of the tagging gradients, the RF and gradient parameters given below, an assumed T2 of 200 ms for arterial blood, and neglecting T1 decay. We note that using unipolar transverse gradient pulses for vessel encoding (graph 1604) can provide similar encoding functionality, but with two differences. First, the tagging curve as a function of the location between fully inverted and unperturbed vessels has a different shape (graph 1604). This curve (1610 or 1612) is very well fit using three Fourier coefficients, and is given by:

$$\Delta M_Z = 2.092 \cos(\theta) - 0.322 \cos(3\theta) + 0.053 \cos(5\theta), \quad [8]$$

where h is the phase along the periodic function. SNR efficiency in VEASL can be calculated, and is maximized using Hadamard encoding. Because the unipolar encoding curve of 1604 is more weighted towards ±1 than that of bipolar encoding (1602), unipolar encoding more closely approximates Hadamard encoding steps, and the overall SNR may be higher. Second, for unipolar encoding, resonance offsets at the tagging location result in a simple shift in the tagging curve, which does not affect the overall tagging efficiency and SNR, as opposed to the decrease in tagging efficiency that is seen with resonance offset in the bipolar case (FIG. 16). For these reasons some implementations may advantageously use the unipolar approach. In order for the RF pulses to follow the phase of the spins in a vessel to be inverted, the additional phase $\phi_i$ is given by $\phi_i = i\pi a = \lambda$, where i is the pulse number, a is the projection of the vector from isocenter to the vessel onto the direction of encoding, and $\lambda$ is encoding wavelength. For the original alternating gradient method, $\phi_i = (i \% 2)\pi a/\lambda$, where % represents the integer modulus function.

Five healthy subjects were studied in a General Electric MR750 3T scanner, using a commercial 8-channel head RF coil, under a protocol approved by the local IRB. MR angiograms were acquired and were used to select the four tagging planes shown in FIG. 17. Tagging plane Location A 1708 features a trapezoidal arrangement of internal carotid and vertebral arteries, has relatively straight arterial segments, and allows for the possibility of separately tagging the two vertebral arteries. Location B 1706 has an anatomically very consistent arrangement of carotid and basilar arteries, but has tortuous segments nearby and typically large resonance offsets. Locations C 1704 and D 1702 are two candidate locations for tagging above the Circle of Willis (CoW) that may allow for tagging of anterior, middle, and posterior cerebral arteries. Between these two locations the anterior cerebral artery runs nearly straight posterior-anterior and is difficult to tag.

At each of these tagging locations, the same 60 pairs of encoding steps were acquired, with random orientation, random phase θ, and random wavelength λ ranging from 15 to 85 mm, in addition to two pairs of non-vessel encoded steps for a total of 124 TR periods per scan. The random encoding steps were generated once and the same encodings used for every subject. For the second of each pair of encoding steps, the RF phase was alternated between 0 and 180 degrees relative to the first step, such that a difference signal between the pair removes static tissue signal and leaves a symmetrical dependence of the ASL signal upon vessel location, as shown in FIG. 16 (graph 1604). Scan parameters were: single shot gradient echo spiral acquisition with $64^2$ matrix, 22 cm FOV, nine 8 mm slices with 2 mm spacing, spatial spectral excitation, 2 μs sampling, 1.6 s tag duration, 800 μs Hamming shaped pulses with 1.4 ms spacing, tagging gradients with 8 mT/m amplitude and 0.6 mT/m mean value, 1 s post labeling delay, and 3 s TR.

Images were subtracted pairwise, resulting in 61 difference images, one without transverse encoding averaged from the two pairs of non-encoded scans. For a uniform array of assumed vessel locations spanning ±64 mm with 2 mm spacing in both X and Y directions, and resonance offsets spanning ±220 Hz with 11 Hz spacing, the theoretical ASL signal across encoding steps was calculated using the random but known encoding parameters and assuming the response of graph 1604. This generates a matrix that maps X and Y vessel coordinates and Frequency (XYF) space into 61 dimensional ASL signal space. For each voxel in the data, the correlation coefficient (CC) between the acquired signal and the theoretical ASL signal from every XYF location was calculated, and the point in XYF space corresponding to the highest CC (CCmax) was assigned to that voxel. For this vessel detection step, images were down sampled to $32^2$ using a 2×2 box shaped kernel to speed up the processing. The choice of 2 mm spacing in XY, and 11 Hz spacing in F is somewhat arbitrary. It is not the resolution in these dimensions, but simply needs to be fine enough so that correlation maxima (CCmax) in XYF space are not missed. Finer spacing than for identifying vessels is not likely to be useful, and increases computation time. Processing time for one scan (7 slices, 124 images of each) was less than one minute running in Matlab on an 8-core Linux server.

Results

Figure 18:
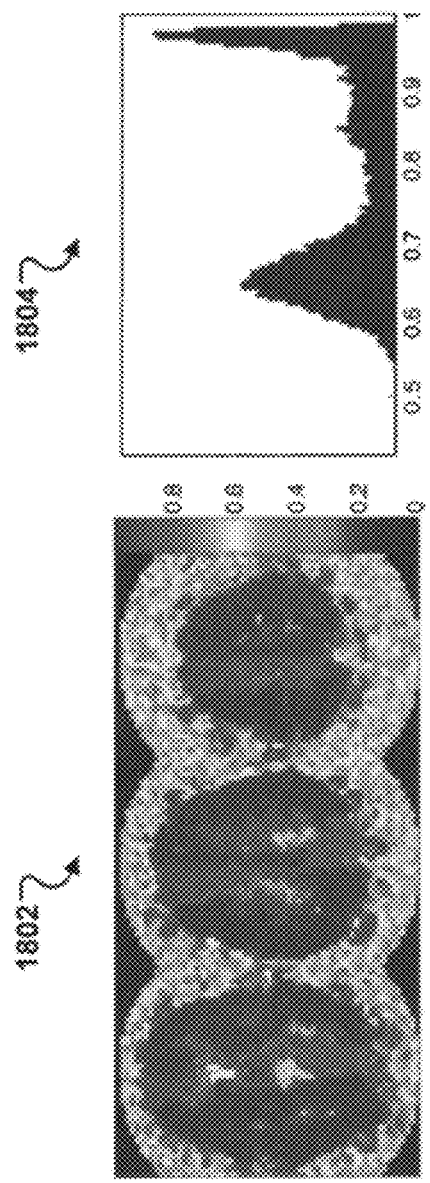
FIG. 18 shows maximum correlation coefficient (CCmax) between signal from each voxel and predicted signal from any point in the XYF tagging space. Left A map of CCmax shows high values in gray matter. In this subject, both the right anterior cerebral and the left posterior cerebral artery territories receive mixed supplies, and CCmax is lower in these areas. Note the high CCmax areas outside the brain, which correspond to extracranial vessels. Right A histogram of CCmax values shows a peak near 0.65 which corresponds to noise voxels. A CCmax threshold of 0.8 was used in this study to identify voxels that fit the signal model well, and were used to detect source vessels.
Figure 19:
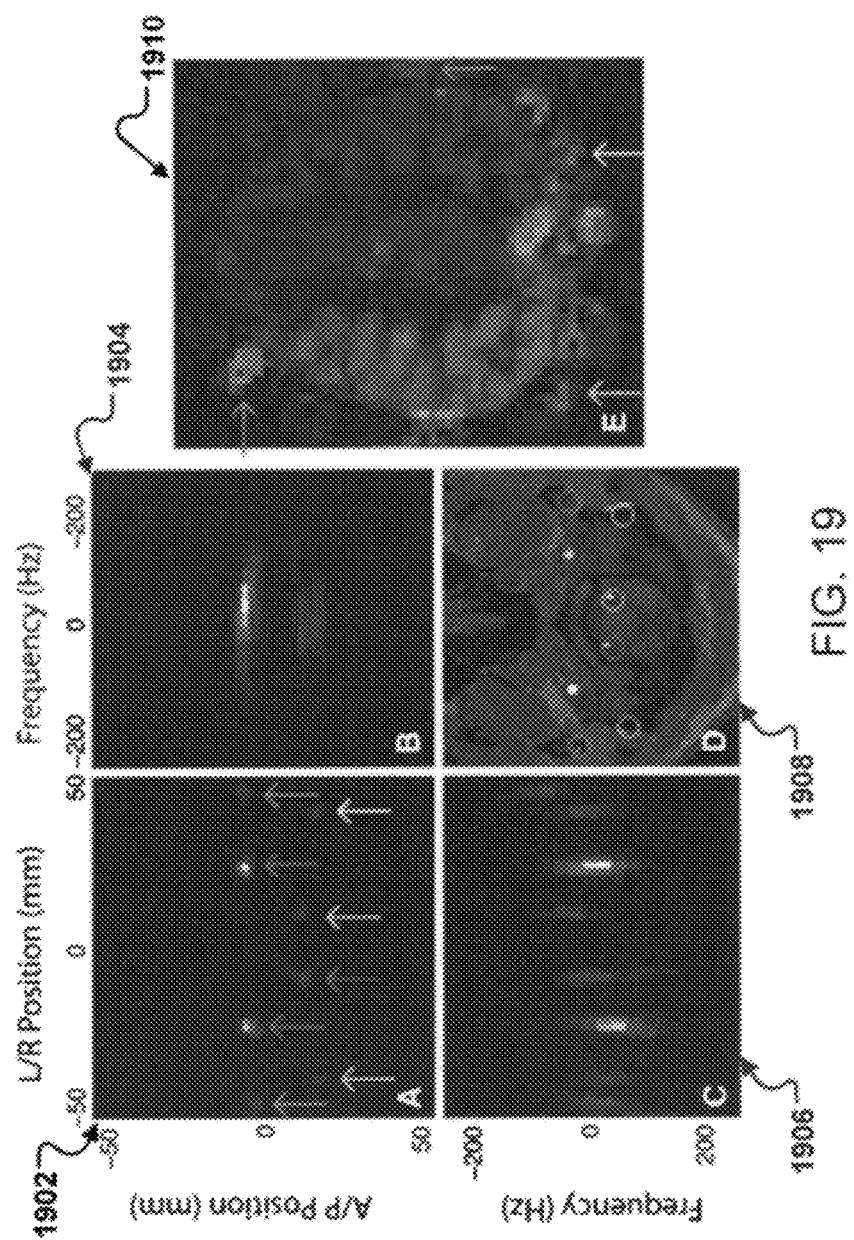
FIG. 19 shows an example detection of source vessels, showing three orthogonal projections of 3D histogram of voxels projected into XYF space. (A) Projection onto XY plane. (B) Projection onto FY plane; (C) Projection onto XF plane. Peaks in these projections correspond to source vessels. (D) Eight peaks seen in (A) shown as circles, superimposed on an anatomical image of the tagging plane. These eight vessels correspond to two carotid arteries, two vertebral arteries, and four extracranial arteries. (E) Territories mapped using the same color scheme as the circles in (D) with extracranial territories increased in brightness by a factor of three for visibility. Extracranial territories were detected in all subjects, and are indicated by arrows. Right anterior cerebral territory receives mixed left and right carotid contributions, resulting in a purple color (a mix of red and blue).

A map of CCmax (1802), and a histogram 1804 thereof are shown in FIG. 18. The histogram clearly shows a bimodal distribution, with the lower peak corresponding to areas of low or no perfusion (including noise outside the head), and the higher peak corresponding to voxels with high perfusion and good fit to the signal model. Voxels with CCmax>0.8 were used for estimation of vessel locations, and histograms of those voxels in XYF space were constructed. An example, with three orthogonal projections of this 3-dimensional histogram are shown in FIG. 19. Clusters in this histogram were identified manually, and the centroids of the clusters represent estimated vessel locations and resonance offsets in the tagging plane. These vessels locations were used to construct an encoding matrix and used in a linear analysis, allowing for detection and estimation of mixed supplies where they occur. In the color vascular territory maps shown, the brightness is proportional to the total flow from all feeding arteries, and the color is derived from the colors assigned arbitrarily to each vessel, mixed in RGB color space weighted by the relative contribution from each vessel.

In the example shown in FIG. 19, eight clusters are apparent in the projection of the XYF histogram onto the XY plane (1902). The locations of these clusters are superimposed on an anatomical image of the tagging plane in 1908, and show that the central four vessels are the internal carotid and vertebral arteries. The left and right carotid arteries are designated blue and red, respectively, and the purple color of the right anterior cerebral artery territory in 1910 indicates that in this subject, that territory receives a mixed supply from left and right carotids. This is consistent with data from this subject using conventional (non-random) VEASL, and MR angiography that shows a patent anterior communicating artery (data not shown). The measured resonance offsets (horizontal axis in 1904 and vertical axis in 1906) are relatively small among these four vessels, ranging from −18 to 24 Hz. In addition to the four intracranial arteries, four peaks in the histogram, indicated by the arrows in 1902, presumably correspond to the temporal and occipital branches of the external carotid arteries. The vascular territories of these four arteries are indicated by arrows with corresponding colors in 1910. These territories have been increased in brightness by a factor of three for visibility, and are likely mainly cutaneous arteries, many of which are blurred by the spiral acquisition. External carotid territories were detected consistently in all scans.

Figure 20:
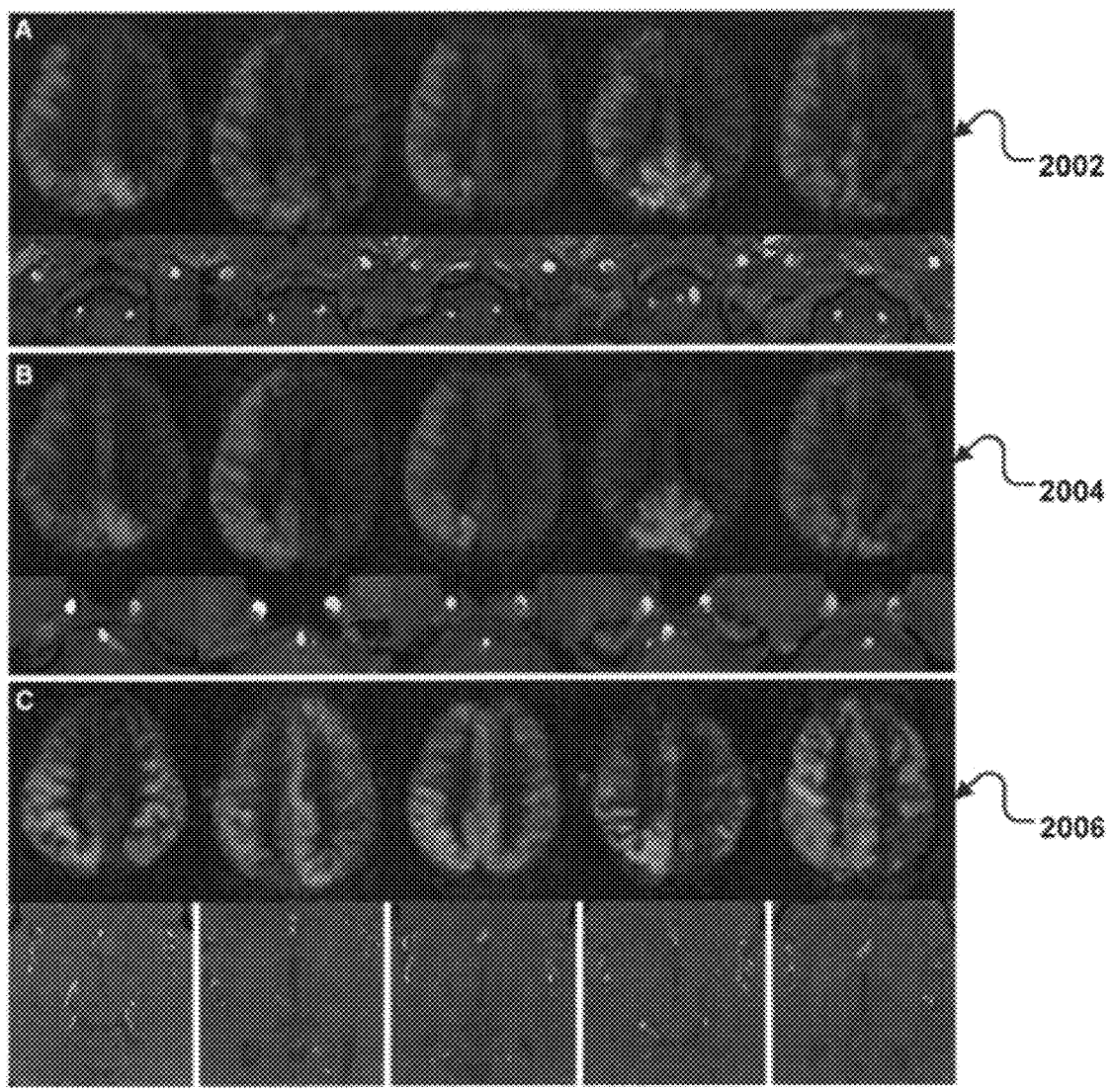
FIG. 20 shows estimated source vessels and vascular territories for 5 subjects (left to right). From Top tagging planes (A) (B) and (C) (see FIG. 17). Below each territory map, an anatomical image of the tagging plane is shown, with a projection of the histogram in XYF space superimposed in magenta. Peaks in this histogram are identified with colored asterisks, with colors corresponding to the vascular territory map.

FIG. 20 shows the vascular territories of the intracranial arteries for all five subjects, for three of the four tagging planes. Only one of the nine slices is shown. The highest tagging plane (FIG. 17) yielded results similar to plane c 1804, and is not shown. In FIG. 20, the relevant region of the tagging plane is shown below each territory map, with the XY projection of the XYF histogram overlayed on the anatomical image in magenta. Vessels locations were chosen manually at the peaks of the histogram, and are indicated by asterisks, with colors corresponding to associated vascular territory. In all subjects, separate peaks in the histogram corresponding to left and right vertebral arteries were seen (top row 2002), although the number of voxels appearing at each vertebral location can be small. In row 2004, subjects 1 and 3, the localization of the right carotid artery was significantly off, but the nearest peak in the XY histogram did correctly identify the vascular territory. The resonance offsets at this tagging plane can be very large, as the vessels are close to the sphenoid sinus, and it was suspected that the resonance offset could affect the vessel localization. However the offsets measured at the two mislocalized carotid arteries were 21 Hz and 75 Hz, while larger offsets were measured in other subjects. For example, offsets of 214 Hz, 184 Hz, and 227 Hz were measured for subject 2 in this plane, and the localization in that subject was good. For tagging above the CoW (row 2006), multiple vessels, including anterior and posterior cerebral arteries, and several branches of the middle cerebral arteries are consistently detected.

The data shown here demonstrates that randomly encoded VEASL data can provide sufficient information to decode source vessel locations. Using a threshold on CCmax was an effective means of identifying voxels that will provide accurate vessel localization. The simple VEASL signal model used here, which assumes a single response function independent of flow velocity, is accurate enough to provide a fit to the data with CC>0.8, and often exceeding 0.95. We initially used signal variance across encodes as a parameter to select voxels for source analysis, but found that cardiac pulsations, which generate large and synchronous signal modulation across many voxels, often cluster to a spurious point in XYF space, leading to identification of a vessel that does not exist. The use of a CCmax threshold effectively reduces this problem, as we have not found vascular pulsations to pass the threshold. Because of the large number of points in XYF space (65×65×41), the CC between even pure noise and the best fitting signal model is relatively high (i.e. the peak centered around 0.65 in FIG. 18). For smaller numbers of encoding steps, CCmax for noise is even higher, and was found to be 0.75 with 30 pairs of encoding steps, and 0.90 with 15 pairs of encodings. Thus, for the CCmax threshold of 0.8 used in this study, approximately 60 pairs of encoding steps (as used in this study) are required to provide a clear separation in CCmax between well perfused voxels and noise.

In areas that receive mixed supply, the VEASL signal should not correlate well with the signal model associated with any single point in XYF space. The potential for this to compromise vessel detection is clearly present when tagging the vertebral arteries, as they join to form the basilar artery prior to entering the CoW. Apparently in all five of the subjects studied, there is a sufficient lack of mixing in at least some portion of the posterior territory that both vertebral arteries could be identified. This is consistent with previous results in which a general lack of complete vertebral mixing was found, but it is not yet known whether this is reliably the case across the population.

The present disclosure demonstrates that it is not necessary to identify source vessels within the tagging plane prior to VEASL scanning. However, only for verification purpose, an angiogram was used to choose tagging planes that contain relatively straight and well separated vessel segments. In some implementations, choosing a tagging plane based on anatomical landmarks, as is commonly done for conventional PCASL, is sufficient for random VEASL. In one advantageous aspect, random VEASL may reduce the required user input for scan prescription, which may save time, but the more important goal is to detect all source vessels. An example is the detection of an external carotid collateral in a patient with cerebrovascular disease such as stroke or carotid stenosis, and it is promising that in this study, the territories of extracranial arteries were consistently detected.

The SNR efficiency of random VEASL is in principle similar to that of multiphase PCASL. While multiphase PCASL uniformly samples the tagging efficiency curve of FIG. 16 to provide insensitivity to resonance offsets, random VEASL randomly samples the same curve, but with a different random sampling pattern for each point in the tagging plane. The SNR efficiency can be calculated for any given encoding matrix, and depends on proximity of other detected vessels. If two vessels are close to one another in XYF space, this translated into a poorly conditioned encoding matrix and noise amplification in the decoding process. For vessels that are far apart, the encoding matrix is well conditioned, and the SNR efficiency approaches the RMS value of the tagging efficiencies of the encoding steps. For conventional PCASL with perfect tagging efficiency and no resonance offset the SNR efficiency is 1. If the tagging efficiency curve was a simple sinusoid, then the SNR efficiency for either densely sampled MP-PCASL or random VEASL would be $1/\sqrt{2}=0.707$, as this is the RMS value of a sin function. For the calculated curves 1610, 1612, the RMS value is slightly higher (0.74), which is identical to the SNR efficiency calculated through the decoding matrix for distant vessels. Calculations show that the SNR efficiency falls to half of this value (0.37) due to noise amplification when two vessels are 6 mm apart. More complete characterization of the SNR behavior of random VEASL is currently underway. Localization of the decoded vascular sources was accurate in most but not all cases.

The vessel locations in the disclosed experiments could also be chosen by hand at the local peaks of the histogram of voxels in XY tagging plane space. For most of the cases, particularly below the CoW, a simple threshold detected the same vessel locations, but above the CoW the identification of vessels is more uncertain. The automation of vascular territory detection is also possible. Such an automated detection more fully realizes the potential of automated vascular territory mapping without a priori knowledge of vessel locations. In some implementations, clustering methods in any combination of three spaces may be used: physical brain space, as territories tend to be contiguous in the brain; raw data space, where the noise often has predictable characteristics; and XYF tagging plane space, where the vessels are inherently sparse. Bayesian estimation methods have also been applied with success to the general problem of VEASL data processing, and can be adapted to the methods described here.

It will be appreciated that in the results presented above, it has been demonstrated that randomly encoded VEASL allows for the unique identification of source vessel locations and resonance offsets. In some implementations, this method may provide important and specific information for the diagnosis and management of cerebrovascular disease, tumors, and other conditions where collateral or aberrant flow patterns may be present and it is important to identify the arterial supply.

Figure 21:
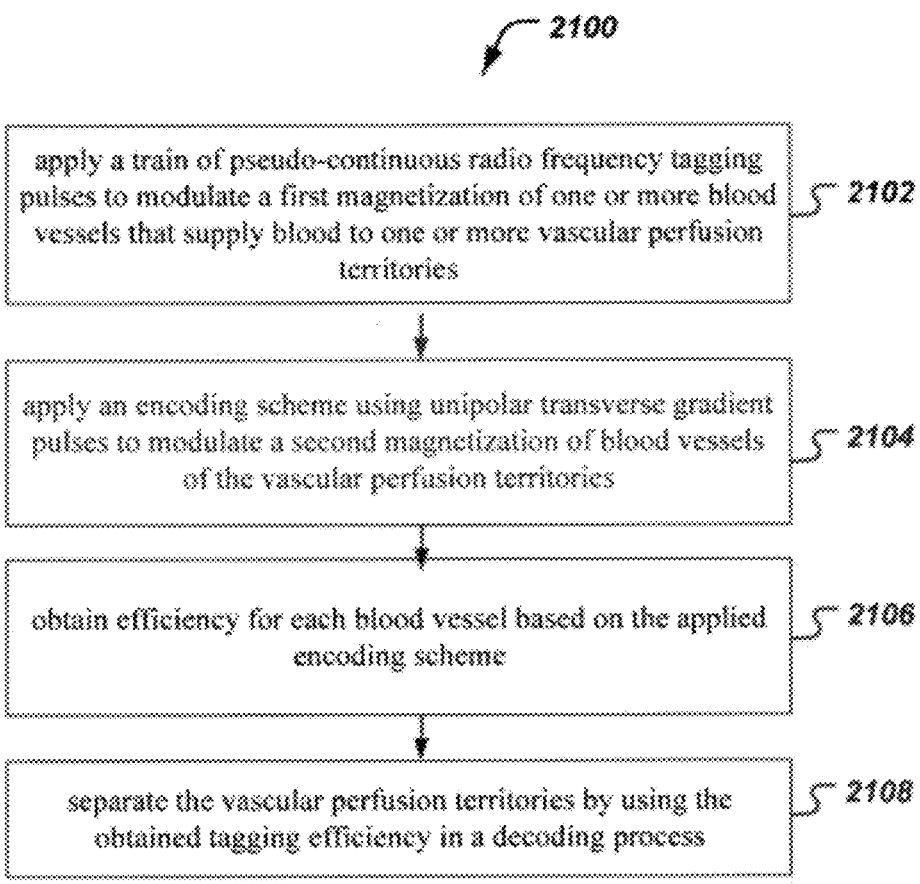
FIG. 21 is a flow chart representation of an MRI process.

FIG. 21 is a flow chart representation of a process 2100 for mapping vascular perfusion territories. The process 2100 may be implemented during laboratory research work or for patient diagnostics and treatment.

At 2102, a train of pseudo-continuous radio frequency tagging pulses is applied to modulate a first magnetization of one or more blood vessels that supply blood to one or more vascular perfusion territories. For example, in some implementations, this operation may include selecting and tagging one or more of the blood vessels using arterial spin labeling. In some implementations, pulses of magnetic field gradients may be applied across the tagging plane between the train of pseudo-continuous RF pulses, resulting in the generation of phase shifts in the one or more blood vessels. In some implementations, two or more of the blood vessels may be differentially encoded within the tagging plane using a modified pseudo-continuous arterial spin labeling.

At 2104, an encoding scheme using unipolar transverse gradient pulses is applied to modulate a second magnetization of blood vessels of the vascular perfusion territories. In some implementations, the encoding scheme may comprise a Hadamard encoding scheme. In some implementations, the encoding scheme may be applied by optimizing Signal to Noise Ratio of the measurement.

At 2106, tagging efficiency for each blood vessel is obtained, based on the applied encoding scheme. In some implementations, the obtaining may be in the form of measuring or calculating. For example, in some implementations, the tagging efficiency may be measured on a per-vessel basis to improve the decoding process. In some implementations, the process 2100 may further include quantitatively measuring a perfusion of each vascular perfusion territory. In some implementations, the tagging efficiency may be measured by clustering.

At 2108, the vascular perfusion territories are separated by using the obtained tagging efficiency in a decoding process. The separation of vascular perfusion territories has also been previously described in U.S. patent application Ser. No. 12/111,133, entitled "Mapping of Vascular Perfusion Territories," filed on Apr. 28, 2008, which is incorporated by reference in its entirety in the present document.

Figure 22:
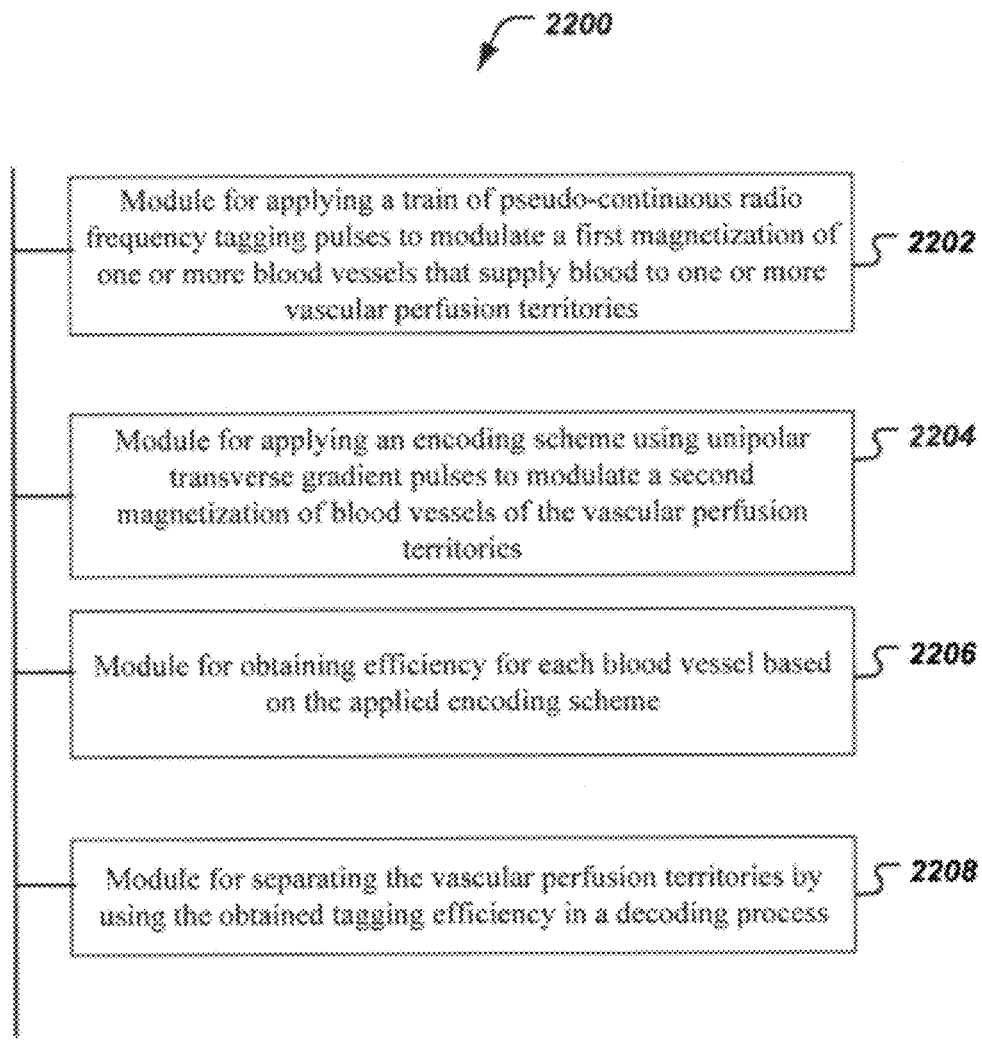
FIG. 22 is a block diagram representation of an MRI apparatus.

FIG. 22 depicts a block diagram representation of an MRI system 2200. The module 2202 is for applying a train of pseudo-continuous radio frequency tagging pulses to modulate a first magnetization of one or more blood vessels that supply blood to one or more vascular perfusion territories. The module 2204 is for applying an encoding scheme using unipolar transverse gradient pulses to modulate a second magnetization of blood vessels of the vascular perfusion territories. The module 2206 is for obtaining efficiency for each blood vessel based on the applied encoding scheme. The module 2208 is for separating the vascular perfusion territories by using the obtained tagging efficiency in a decoding process. The apparatus 2200 and modules 2202, 2204, 2206, 2208 may further be configured to implement some of the techniques disclosed in this document.

Figure 23:
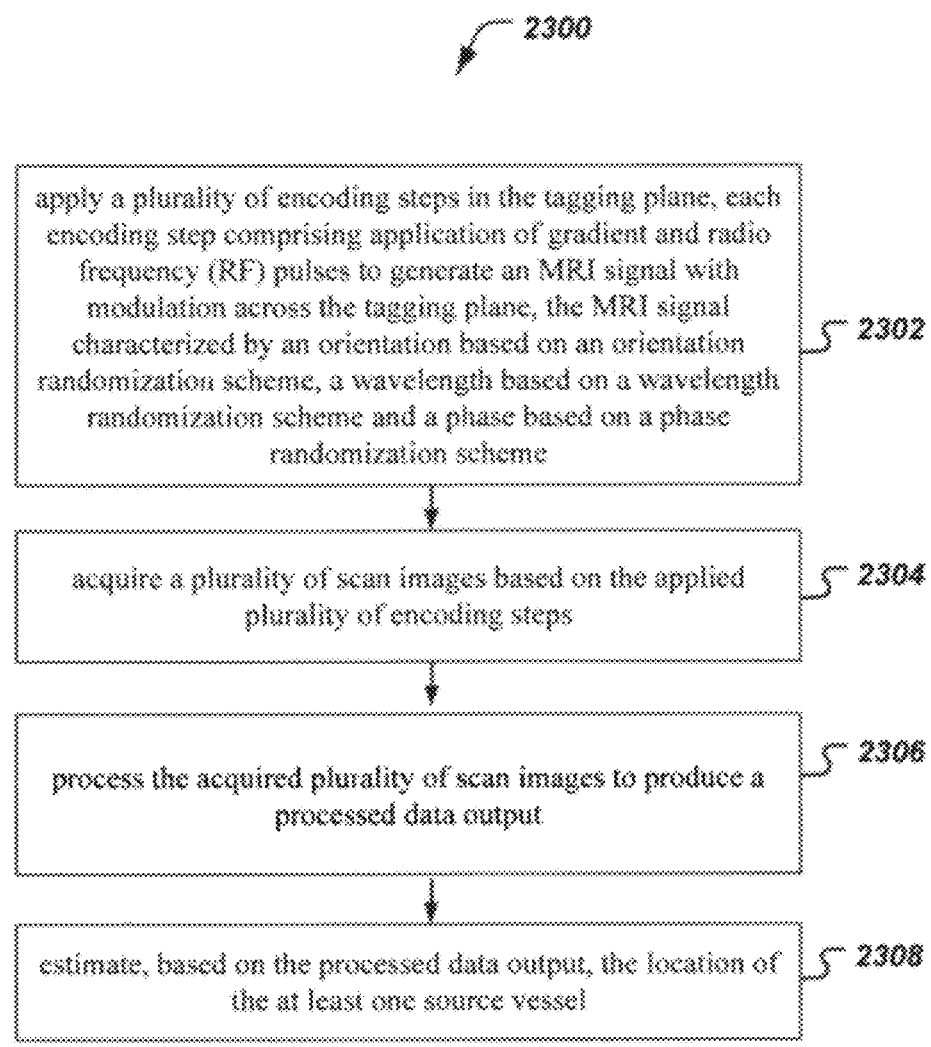
FIG. 23 is a flow chart representation of an MRI process.

FIG. 23 is a flow chart representation of a process 2300 of estimating location of a source vessel in the tagging plane of a subject.

At 2302, a plurality of encoding steps is applied in the tagging plane. Each encoding step comprises the application of gradient and radio frequency (RF) pulses to generate an MRI signal with modulation across the tagging plane. The MRI signal is characterized by an orientation based on an orientation randomization scheme, a wavelength based on a wavelength randomization scheme and a phase based on a phase randomization scheme. In some implementations, the orientation randomization scheme includes randomly selecting an orientation angle between 0 and 360 degrees. In some implementations, the phase randomization scheme includes randomly selecting a phase between 0 and 360 degrees. In some implementations, the wavelength randomization scheme includes randomly selecting a wavelength between a minimum value and a maximum value. As previously discussed, wavelengths may be between 15 mm and 85 mm. As previously discussed, in some implementations, the phase randomization scheme includes selecting phases in encoding step pairs such that a first phase of a first encoding step from the encoding step pair is randomly selected and a second phase of a second encoding step from the encoding step pair is selected to be 180 degrees away from the first phase.

At 2304, a plurality of scan images is acquired based on the applied plurality of encoding steps.

At 2306, the acquired plurality of scan images is processed to produce a processed data output.

At 2308, based on the processed data output, the location of the source vessel is estimated. As previously discussed, in some implementations, the processing includes pairwise subtracting scan images from the acquired plurality of scan images. In some implementations, the estimation operation includes generating a plurality of possible outputs based on an encoding scheme and assumed vessel locations in the tagging plane, comparing the processed data output with results from a plurality of possible theoretical image signals based on the encoding scheme and assumed vessel locations and selecting the location of the vessel to correspond to an assumed vessel location at which the comparison operation shows a maximum correlation.

In some implementations, the process 2300 may further include measuring a resonance offset of the source vessel.

Figure 24:
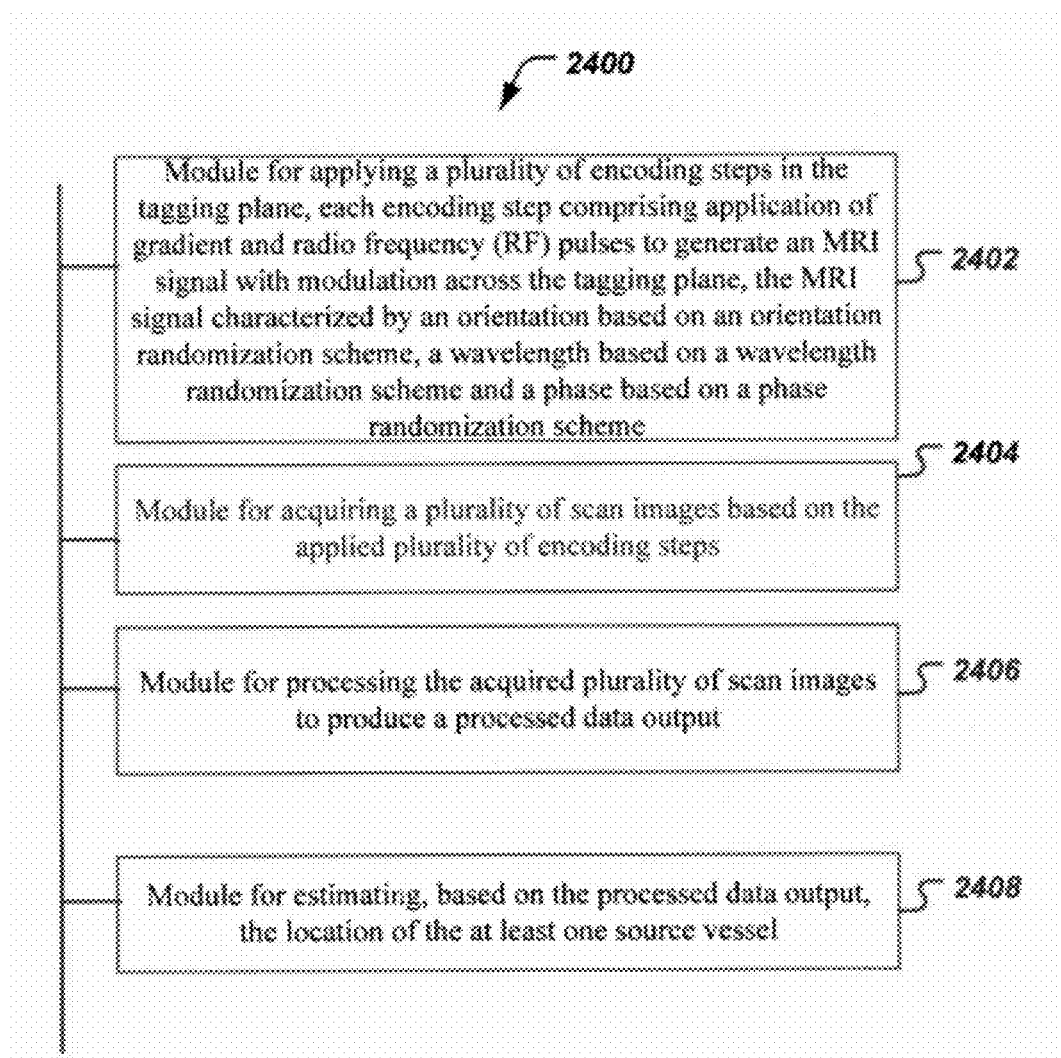
FIG. 24 is a block diagram representation of an MRI apparatus.

FIG. 24 is a block diagram representation of an apparatus 2400 for magnetic resonance imaging. The module 2402 is for applying a plurality of encoding steps in the tagging plane, each encoding step comprising application of gradient and radio frequency (RF) pulses to generate an MRI signal with modulation across the tagging plane, the MRI signal characterized by an orientation based on an orientation randomization scheme, a wavelength based on a wavelength randomization scheme and a phase based on a phase randomization scheme. The module 2404 is for acquiring a plurality of scan images based on the applied plurality of encoding steps. The module 2406 is for processing the acquired plurality of scan images to produce a processed data output. The module 2408 is for estimating, based on the processed data output, the location of the at least one source vessel. The apparatus 2400 and modules 2402, 2404, 2406, 2408 may further be configured to implement some of the techniques disclosed in this document.

The subject technology is illustrated, for example, according to various aspects described below. Numbered clauses are provided below for convenience. These are provided as examples, and do not limit the subject technology.

1. A computer program product, embodied on a computer-readable medium, operable to cause a data processing apparatus to perform operations comprising generating a train of pseudo-continuous radio frequency tagging pulses to modulate magnetization of one or more blood vessels that supply one or more vascular perfusion territories, performing an encoding scheme using unipolar gradient pulses to modulate magnetization of blood vessels of the vascular perfusion territories, obtaining a tagging efficiency for each blood vessel based on the applied encoding scheme; and separating the vascular perfusion territories by using the obtained tagging efficiency in a decoding process.

2. The computer program product of clause 1, wherein the applying the train of pseudo-continuous radio frequency tagging pulses comprises selecting and tagging one or more of the blood vessels using arterial spin labeling.

3. The computer program product of clause 2, the method further including applying pulses of magnetic field gradients across the tagging plane between the train of pseudo-continuous radio frequency pulses to generate phase shifts in the one or more blood vessels.

4. The computer program product of clause 3, the method further comprising differentially encoding two or more of the blood vessels within the tagging plane by using a modified pseudo-continuous arterial spin labeling.

5. The computer program product of clause 1, the method further comprising applying a single labeling gradient waveform in a direction of blood flow with non-zero mean for the tag and control conditions.

6. The computer program product of clause 1, wherein the applying the encoding scheme comprises using a Hadamard encoding scheme.

7. The computer program product of clause 1, wherein the obtaining the tagging efficiency comprises measuring the tagging efficiency on a per-vessel basis to improve the decoding process.

8. The computer program product of clause 1, the method further comprising quantitatively measuring a perfusion of each vascular perfusion territory.

9. The computer program product of clause 1, the method further comprising measuring and quantifying a contribution of the one or more of the blood vessels to the perfusion of each voxel.

10. The computer program product of clause 1, wherein applying the encoding scheme comprises optimizing a signal-to-noise ratio.

11. The computer program product of clause 1, the method further comprising mapping the measured tagging efficiencies to blood vessel coordinates.

12. The computer program product of clause 1, wherein measuring the tagging efficiencies comprises measuring the tagging efficiencies by clustering.

The subject technology is illustrated, for example, according to various aspects described below. Numbered clauses are provided below for convenience. These are provided as examples, and do not limit the subject technology.

1. An apparatus for magnetic resonance imaging (MRI) for estimating a location of at least one source vessel in a tagging plane of a subject, the apparatus comprising a first set of coils that apply a plurality of encoding steps in the tagging plane, each encoding step comprising application of gradient and radio frequency (RF) pulses to generate an MRI signal with modulation across the tagging plane, the MRI signal characterized by an orientation based on an orientation randomization scheme, a wavelength based on a wavelength randomization scheme and a phase based on a phase randomization scheme, a second set of coils that acquire a plurality of scan images based on the applied plurality of encoding steps, and a processor configured to process the acquired plurality of scan images to produce a processed data output, and estimate, based on the processed data output, the location of the at least one source vessel.

2. The apparatus of clause 1, wherein the orientation randomization scheme includes randomly selecting an orientation angle between 0 and 360 degrees.

3. The apparatus of clause 1, wherein the phase randomization scheme includes randomly selecting a phase between 0 and 360 degrees.

4. The apparatus of clause 1, wherein the wavelength randomization scheme includes randomly selecting a wavelength between a minimum value and a maximum value.

5. The apparatus of clause 4, wherein the minimum value is 15 mm and the maximum value is 85 mm.

6. The apparatus of clause 1, wherein the phase randomization scheme includes selecting phases in encoding step pairs such that a first phase of a first encoding step from the encoding step pair is randomly selected and a second phase of a second encoding step from the encoding step pair is selected to be 180 degrees away from the first phase.

7. The apparatus of clause 1, wherein the processing operation includes pairwise subtracting scan images from the acquired plurality of scan images.

8. The apparatus of clause 1, wherein the processor is further configured to generate a plurality of possible outputs based on an encoding scheme and assumed vessel locations in the tagging plane, compare the processed data output with results from a plurality of possible theoretical image signals based on the encoding scheme and assumed vessel locations and facilitate selection the location of the vessel to correspond to an assumed vessel location at which the comparison operation shows a maximum correlation.

9. The apparatus of clause 1, further comprising an offset measurer that measures a resonance offset of the at least one source vessel.

The subject technology is illustrated, for example, according to various aspects described below. Numbered clauses are provided below for convenience. These are provided as examples, and do not limit the subject technology.

1. A magnetic resonance imaging (MRI) apparatus for estimating a location of at least one source vessel in a tagging plane of a subject, the method comprising means for applying a plurality of encoding steps in the tagging plane, each encoding step comprising application of gradient and radio frequency (RF) pulses to generate an MRI signal with modulation across the tagging plane, the MRI signal characterized by an orientation based on an orientation randomization scheme, a wavelength based on a wavelength randomization scheme and a phase based on a phase randomization scheme, means for acquiring a plurality of scan images based on the applied plurality of encoding steps, means for processing the acquired plurality of scan images to produce a processed data output and means for estimating, based on the processed data output, the location of the at least one source vessel.

2. The apparatus in clause 1, wherein the orientation randomization scheme includes randomly selecting an orientation angle between 0 and 360 degrees.

3. The apparatus in clause 1, wherein the phase randomization scheme includes randomly selecting a phase between 0 and 360 degrees.

4. The apparatus in clause 1, wherein the wavelength randomization scheme includes randomly selecting a wavelength between a minimum value and a maximum value.

5. The apparatus in clause 4, wherein the minimum value is 15 mm and the maximum value is 85 mm.

6. The apparatus in clause 1, wherein the phase randomization scheme includes selecting phases in encoding step pairs such that a first phase of a first encoding step from the encoding step pair is randomly selected and a second phase of a second encoding step from the encoding step pair is selected to be 180 degrees away from the first phase.

7. The apparatus in clause 1, wherein the means for processing includes means for pairwise subtracting scan images from the acquired plurality of scan images.

8. The apparatus in clause 1, wherein the means for estimating includes means for generating a plurality of possible outputs based on an encoding scheme and assumed vessel locations in the tagging plane, means for comparing the processed data output with results from a plurality of possible theoretical image signals based on the encoding scheme and assumed vessel locations, means for selecting the location of the vessel to correspond to an assumed vessel location at which the comparison operation shows a maximum correlation.

9. The apparatus in clause 1, further comprising: means for measuring a resonance offset of the at least one source vessel.

10. A computer program product having code stored thereon, the code, when executed, causing a processor to implement a technique recited in claims 1 to 9.

It will be appreciated that techniques have been disclosed for estimating locations of blood vessels in the tagging plane of a subject during MRI, without any a priori knowledge of the locations or the number of blood vessels in the tagging plane. In one aspect, randomized waveforms are applied to the subject and the resulting magnetization is compared with the corresponding results based on assumed blood vessel locations for correlations in the waveforms. The assumed vessel positions that exhibit the best correlation with the observed data are estimating to be the locations of the blood vessel(s) in the tagging place of the subject.

It will further be appreciated that in another aspect, the use of unipolar gradient pulses in MRI is disclosed. In one aspect, the use of unipolar gradient pulses facilitates rotating magnetization spins of the subject in the same direction (e.g., clockwise), thereby adding up off resonance in the tagging plane, thereby increasing the efficiency of MRI.

It will further be appreciated that, in some implementations, the disclosed technique enable estimation of source vessel locations using sixty grid points, compared to close to one thousand grid points that may be required using the conventional techniques. Such improvements in vessel location may translate to reduced operating costs, reduced guess work by medical personnel and/or providing better care to the subject patient by being able to map perfusion blood flows and blood path abnormalities in the subject.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "information carrier" comprises a "machine-readable medium" that includes any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal, as well as a propagated machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a WAN, and the Internet.

The computing system may include clients and servers. A client and server are generally remote from each other and typically interact through a communication network. The relationship of client and server arises by virtue of computer programs running on the respective computers and having a client-server relationship to each other.

In addition to these variations, other modifications are possible and within the scope of the following claims.

What is claimed is:

1. A magnetic resonance imaging (MRI) method for estimating a location of at least one source vessel in a tagging plane of a subject, the method comprising:
   using a first set of coils to apply a plurality of encoding steps in the tagging plane, each encoding step comprising application of gradient and radio frequency (RF) pulses to generate an MRI signal with modulation across the tagging plane, the MRI signal characterized by an orientation based on an orientation randomization scheme, a wavelength based on a wavelength randomization scheme and a phase based on a phase randomization scheme, wherein the phase randomization scheme includes selecting phases in encoding step pairs such that a first phase of a first RF pulse of a first encoding step from a given encoding step pair in the encoding step pairs is randomly selected, and a second phase of a second RF pulse of a second encoding step from the given encoding step pair is selected to be 180 degrees away from the first phase, and wherein a difference signal between the encoding step pair facilitates removing a static tissue signal;

using a second set of coils to acquire a plurality of scan images based on the applied plurality of encoding steps;

processing, using a processor, the acquired plurality of scan images to produce a processed data output; and estimating, using the processor, based on the processed data output, the location of the at least one source vessel.

2. The MRI method in claim 1, wherein the orientation randomization scheme includes randomly selecting an orientation angle between 0 and 360 degrees.

3. The MRI method in claim 1, wherein the phase randomization scheme includes randomly selecting a phase between 0 and 360 degrees.

4. The MRI method in claim 1, wherein the wavelength randomization scheme includes randomly selecting a wavelength between a minimum value and a maximum value.

5. The MRI method in claim 4, wherein the minimum value is 15 mm and the maximum value is 85 mm.

6. The MRI method in claim 1, wherein the processing operation includes pairwise subtracting scan images from the acquired plurality of scan images.

7. The MRI method of claim 1, wherein the estimating the location of the at least one source vessel includes:

generating a plurality of possible outputs based on an encoding scheme and assumed vessel locations in the tagging plane;

comparing the processed data output with results from a plurality of possible theoretical image signals based on the encoding scheme and assumed vessel locations; and selecting the location of the vessel to correspond to an assumed vessel location at which the comparison shows a maximum correlation.

8. The MRI method of claim 1, further comprising:

measuring a resonance offset of the at least one source vessel.

9. An apparatus for magnetic resonance imaging (MRI) that includes a first set of coils, a second set of coils, a processor and a non-transitory computer-readable storage medium storing instructions that when executed by a computer cause the apparatus to estimate a location of at least one source vessel in a tagging plane of a subject:

cause the first set of coils to apply a plurality of encoding steps in the tagging plane, each encoding step comprising application of gradient and radio frequency (RF) pulses to generate an MRI signal with modulation across the tagging plane, the MRI signal characterized by an orientation based on an orientation randomization scheme, a wavelength based on a wavelength randomization scheme and a phase based on a phase randomization scheme, wherein the phase randomization scheme includes selecting phases in encoding step pairs such that a first phase of a first RF pulse of a first encoding step from a given encoding step pair in the encoding step pairs is randomly selected, and a second phase of a second RF pulse of a second encoding step from the given encoding step pair is selected to be 180 degrees away from the first phase, and wherein a difference signal between the encoding step pair facilitates removing a static tissue signal;

cause the second set of coils to acquire a plurality of scan images based on the applied plurality of encoding steps; and cause the processor to:

process the acquired plurality of scan images to produce a processed data output, and estimate, based on the processed data output, the location of the at least one source vessel.

10. The apparatus for MRI in claim 9, wherein the orientation randomization scheme includes randomly selecting an orientation angle between 0 and 360 degrees.

11. The apparatus for MRI in claim 9, wherein the phase randomization scheme includes randomly selecting a phase between 0 and 360 degrees.

12. The apparatus for MRI in claim 9, wherein the wavelength randomization scheme includes randomly selecting a wavelength between a minimum value and a maximum value.

13. The apparatus for MRI in claim 12, wherein the minimum value is 15 mm and the maximum value is 85 mm.

14. The apparatus for MRI in claim 9, wherein the processor is configured to process the acquired plurality of scan images by pairwise subtracting scan images from the acquired plurality of scan images.

15. The apparatus for MRI in claim 9, wherein the processor is configured to estimate the location of the at least one source vessel by:

generating a plurality of possible outputs based on an encoding scheme and assumed vessel locations in the tagging plane;

comparing the processed data output with results from a plurality of possible theoretical image signals based on the encoding scheme and assumed vessel locations; and selecting the location of the vessel to correspond to an assumed vessel location at which the comparison shows a maximum correlation.

16. The apparatus for MRI in claim 9, wherein the apparatus is configured to measure a resonance offset of the at least one source vessel.

\* \* \* \* \*